(12) United States Patent
Mou et al.

(10) Patent No.: US 11,531,015 B2
(45) Date of Patent: Dec. 20, 2022

(54) METHOD OF AIR QUALITY NOTIFICATION

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW); Hsuan-Kai Chen, Hsinchu (TW); Chun-Yi Kuo, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 481 days.

(21) Appl. No.: 16/696,703

(22) Filed: Nov. 26, 2019

(65) Prior Publication Data

US 2020/0173971 A1 Jun. 4, 2020

(30) Foreign Application Priority Data

Nov. 29, 2018 (TW) .................................. 107142802

(51) Int. Cl.
*H04L 67/55* (2022.01)
*G01N 33/00* (2006.01)
(Continued)

(52) U.S. Cl.
CPC ....... *G01N 33/0063* (2013.01); *G01N 1/2273* (2013.01); *H04L 67/55* (2022.05);
(Continued)

(58) Field of Classification Search
CPC ....... H04W 24/00; H04W 4/00; H04W 4/021; H04W 64/003; H04M 2250/12;
(Continued)

(56) References Cited

U.S. PATENT DOCUMENTS 9,194,955 B1 * 11/2015 Fahrner .................. G01S 19/16
10,404,840 B1 * 9/2019 Leung .................. H04L 65/601
(Continued)

FOREIGN PATENT DOCUMENTS

CN 103412086 A 11/2013
CN 104459830 A 3/2015
(Continued)

OTHER PUBLICATIONS

Zhihao, "[Howto do data governance] Environmental audits also need to be handled scientifically, and the Environmental Protection Agency relies on AI to see through the polluting factories", Url: https://www.ithome.com.tw/news/117265, Oct. 9, 2017, 8 page total, with 1st page abstract.

*Primary Examiner* — Joseph Arevalo
(74) *Attorney, Agent, or Firm* — Birch, Stewart, Kolasch & Birch, LLP

(57) ABSTRACT

A method of air quality notification is disclosed. The method includes steps of providing a portable air quality monitoring device for monitoring air quality. The portable air quality monitoring device monitors the ambient air quality at a location in a monitoring period of time to generate a monitoring data, and has a GPS component to generate a position data of the location, both of them can be integrated as a notification data and delivered. A cloud data processing device is provided for receiving the notification data delivered from the portable air quality monitoring device, wherein the notification data is processed, calculated and converted to generate a push data, and the push data is delivered at a push period through a push notification service. A notification receiving device is provided for receiving the push data delivered from the cloud data processing device, so as to display the push data immediately.

19 Claims, 24 Drawing Sheets

(51) Int. Cl.
*G01N 1/22* (2006.01)
*G16Y 20/10* (2020.01)
*G01S 19/13* (2010.01)
*H04L 67/12* (2022.01)

(52) U.S. Cl.
CPC .............. *G01S 19/13* (2013.01); *G16Y 20/10* (2020.01); *H04L 67/12* (2013.01)

(58) Field of Classification Search
CPC .............. H04M 1/04; H04M 1/72403; H04M 1/72445; H04M 1/72469; G01F 1/363; G01F 1/34; G01F 22/02; G01F 9/001; G01F 9/023; G01F 1/36; G01F 23/20; G01F 23/2962; G01F 23/804; G01F 1/00; G01F 1/42; G01F 1/002; G01F 1/44; G01F 1/46; G01F 1/6842; G01F 1/72; G01F 1/74; G01F 1/86; G01F 23/265; G01F 23/268; G01F 25/10; G01F 9/00; G01F 1/115; G01F 1/56; G01F 1/66; G01F 1/663; G01F 1/667; G01F 15/06; G01F 15/063; G01F 15/18; G01F 15/185; G01F 23/00; G01F 23/292; G01F 5/00; G01F 9/02
USPC .......... 455/404.2, 561, 41.3, 39, 420, 456.1, 455/518, 418, 440, 456, 3; 73/655, 146, 73/197, 31.01, 23.2, 1.38, 865.8, 114.68
See application file for complete search history.

(56) References Cited

U.S. PATENT DOCUMENTS

| | | | |
|---|---|---|---|
| 2014/0275850 A1* | 9/2014 | Venkatraman | A61B 5/02416 600/595 |
| 2014/0358012 A1* | 12/2014 | Richards | H04W 4/027 600/479 |
| 2015/0052975 A1 | 2/2015 | Martin | |
| 2015/0077737 A1* | 3/2015 | Belinsky | G01N 15/0211 250/208.2 |
| 2015/0088786 A1* | 3/2015 | Anandhakrishnan | G16H 50/80 706/11 |
| 2015/0116108 A1* | 4/2015 | Fadell | G08B 27/003 340/501 |
| 2016/0084869 A1* | 3/2016 | Yuen | A63B 21/072 73/510 |
| 2016/0125725 A1* | 5/2016 | Sager | G08B 25/005 340/502 |
| 2018/0173706 A1* | 6/2018 | Dev | G06F 16/24565 |
| 2018/0324897 A1* | 11/2018 | Wu | H04W 88/04 |
| 2019/0084369 A1* | 3/2019 | Duan | B60H 1/008 |
| 2019/0086378 A1* | 3/2019 | Holdcroft | G01N 33/0009 |
| 2019/0120196 A1* | 4/2019 | Santoro | F02D 41/064 |
| 2022/0066456 A1* | 3/2022 | Ebrahimi Afrouzi | A47L 9/30 |
| 2022/0091026 A1* | 3/2022 | Scott | G01P 13/045 |

FOREIGN PATENT DOCUMENTS

| | | |
|---|---|---|
| CN | 103607490 B | 2/2017 |
| CN | 108593512 A | 9/2018 |
| JP | 2015-152175 A | 8/2015 |
| TW | M552632 | 12/2017 |
| TW | M562968 U | 7/2018 |
| TW | M567365 | 9/2018 |
| TW | M567862 | 10/2018 |
| TW | I640963 B | 11/2018 |

\* cited by examiner

METHOD OF AIR QUALITY NOTIFICATION

FIELD OF THE INVENTION

The present disclosure relates to a method of air quality notification, and more particularly to a method of air quality notification for monitoring air quality by a portable air quality monitoring device.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these substances in the environment can cause human health problems or can even harm the life. Therefore, it has become an important issue for every country to develop and implement environmental air quality monitoring technology.

Generally, it is feasible to use an environmental sensor to monitor the air quality in the environment. If the environmental sensor is capable of immediately providing people with the monitored information relating to the environment for caution, it may help people escape or prevent from the injuries and influence on human health caused by the exposure of substances described above in the environment. In other words, the environmental sensor is suitably used for monitoring the ambient air in the environment.

Nowadays, a large-scale environmental monitoring base station is provided to monitor the ambient air quality. However, the large-scale environmental monitoring base station is only suitable for monitoring the ambient air quality near the environmental monitoring base station. If the large-scale environmental monitoring base station is used to monitor the air quality in a small area where the human activities exist (e.g., the indoor air quality and the ambient air surrounding us), the monitoring result is usually not accurately and quickly acquired. Consequently, if the environmental sensor could be applied in an electronic device, the air quality can be effectively monitored everywhere and at any time. Namely, the monitored data can be delivered to a cloud database to be constructed and integrated. Therefore, the monitoring accuracy is increased, the air quality can be immediately monitored everywhere and at any time, and the air quality notification mechanism is enabled. In addition, an instant air quality map is also provided to notify the user for consideration for evacuation or the like.

Therefore, there is a need of providing a method of air quality notification for monitoring air quality by a portable air quality monitoring device.

SUMMARY OF THE INVENTION

An object of the present disclosure provides a method of air quality notification for monitoring air quality by a portable air quality monitoring device. The portable air quality monitoring device monitors the ambient air quality at a location at regular intervals of 8 seconds so as to generate a monitoring data. The portable air quality monitoring device has a Global Positioning System (GPS) component to generate the position data of the location. The monitoring data and the position data can be integrated as a notification data by the portable air quality monitoring device, and to be delivered. A cloud data processing device is provided for receiving the notification data, processing, calculating and converting the notification, so that a push data is generated and then delivered at a push period to a notification receiving device through a push notification service. Consequently, the notification receiving device is capable of receiving 3600 air quality information of the address information related to the house number of the location within 8 hours. Meanwhile, the air quality information can be delivered to the user through the push notification service. In this circumstance, the instant information is provided, and the user can be notified to take immediate protective measures to avoid the gas poisoning and the gas explosion.

In accordance with an aspect of the present disclosure, a method of air quality notification is provided. The method includes steps of providing a portable air quality monitoring device for monitoring air quality. The portable air quality monitoring device monitors the ambient air quality at a location in a monitoring period of time to generate a monitoring data, and has a GPS component to generate a position data of the location. The monitoring data and the position data can be integrated as a notification data by the portable air quality monitoring device, and to be delivered. A cloud data processing device is provided for receiving the notification data delivered from the portable air quality monitoring device, wherein the notification data is processed, calculated and converted to generate a push data, and the push data is delivered at a push period through a push notification service. A notification receiving device is provided for receiving the push data delivered from the cloud data processing device, so as to display the push data immediately.

In accordance with another aspect of the present disclosure, a method of air quality notification is provided. The method includes steps of providing a portable air quality monitoring device for monitoring air quality. The portable air quality monitoring device monitors the ambient air quality at a location in a monitoring period of time to generate a monitoring data, and has a GPS component to generate a position data of the location. The monitoring data and the position data can be integrated as a notification data by the portable air quality monitoring device, and to be delivered. A notification receiving device is provided for receiving the notification data delivered from the portable air quality monitoring device. The notification receiving device delivers the notification data to a cloud data processing device. The cloud data processing device receives the notification data, after processing and calculating the notification data, the notification data is converted into a push data. The push data is then delivered at a push period through a push notification service. Finally, the notification receiving device receives the push data delivered from the cloud data processing device, so as to display the push data immediately.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1A:
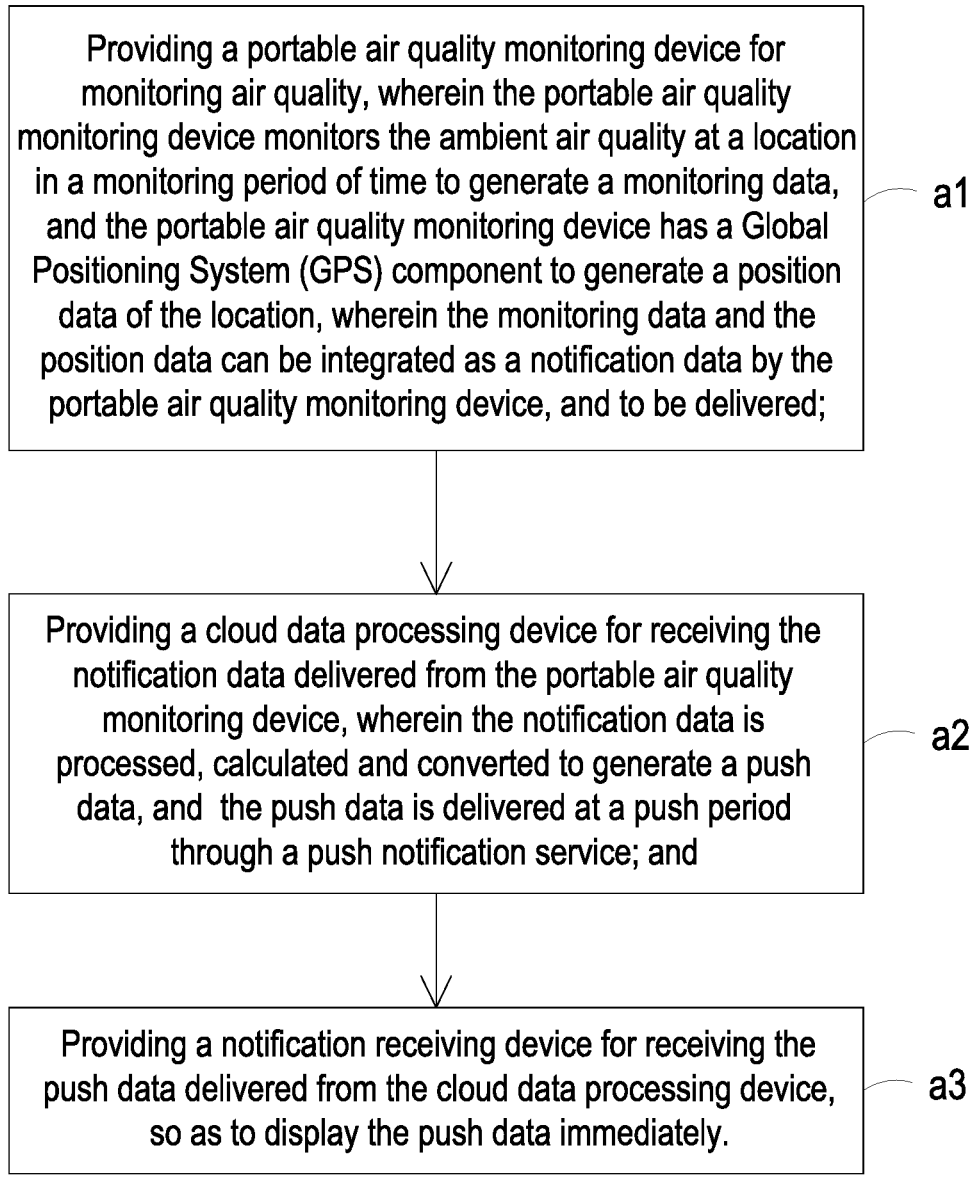
FIG. 1A is a flow chart illustrating a method of providing an air quality notification according to a first embodiment of the present disclosure.

Please refer to FIG. 1A. The present discourse provides a method of providing an air quality notification including the following steps. At the step a1, a portable air quality monitoring device 1 for monitoring air quality is provided. The portable air quality monitoring device 1 monitors the ambient air quality at a location in a monitoring period of time so as to generate a monitoring data. The portable air quality monitoring device 1 has a Global Positioning System (GPS) component 14 to generate the position data of the location of the portable air quality monitoring device 1. The monitoring data and the position data can be integrated as a notification data by the portable air quality monitoring device 1, and to be delivered.

At the step a2, a cloud data processing device 4 is provided for receiving the notification data delivered from the portable air quality monitoring device 1. The cloud data processing device 4 processes and calculates the notification data and converts it into a push data, and then delivers the push data at a push period through a push notification service.

At the step a3, a notification receiving device 5 is provided for receiving the push data delivered from the cloud data processing device 4, so as to display the push data immediately.

Figure 2:
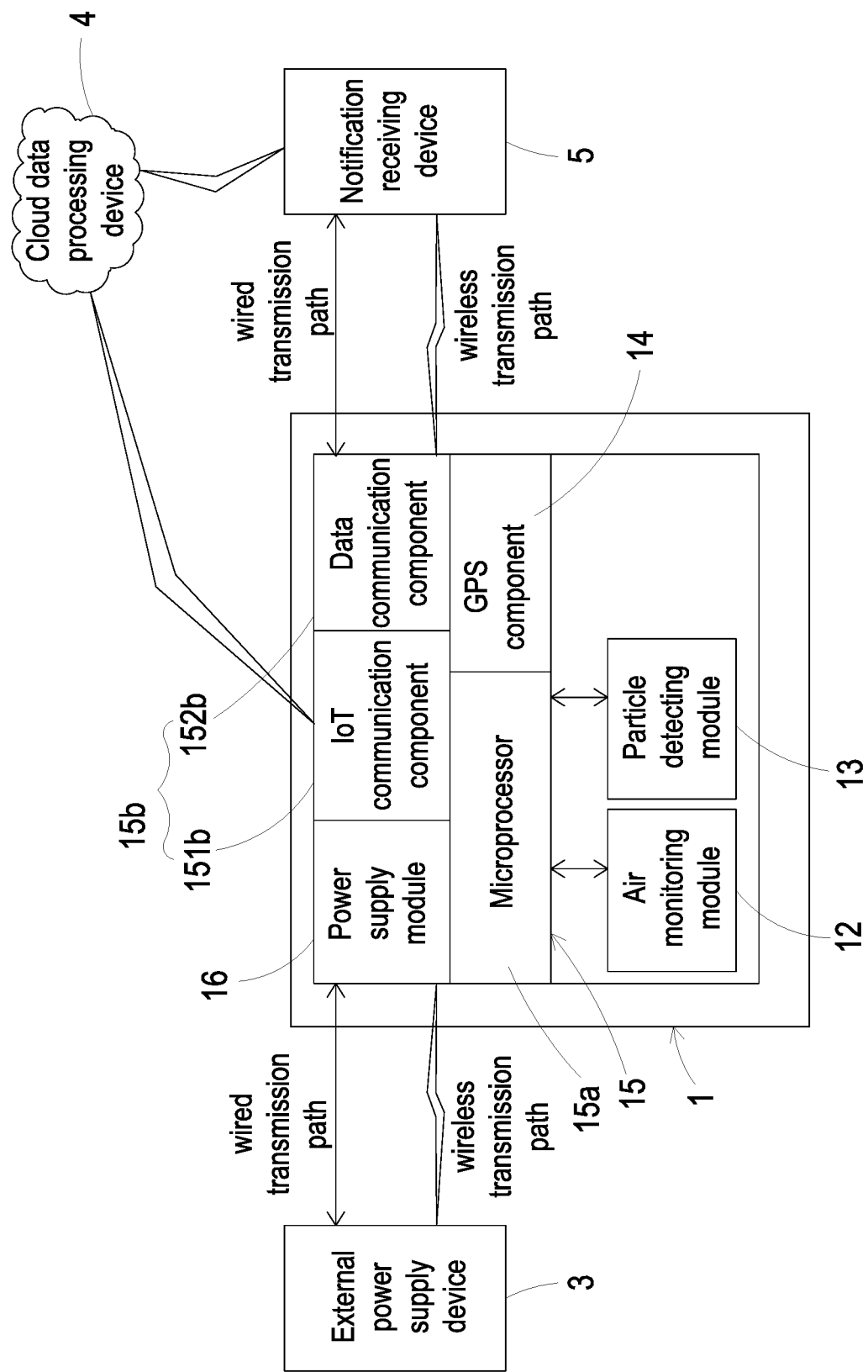
FIG. 2 is a block diagram illustrating a system for providing an air quality notification according to an embodiment of the present disclosure.
Figure 3A:
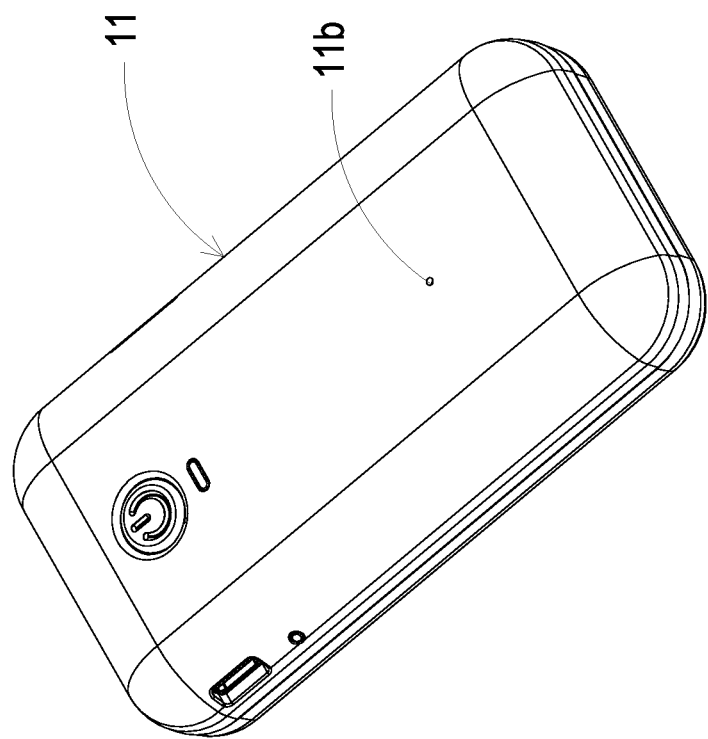
FIG. 3A is a schematic stereo view illustrating a portable air quality monitoring device of FIG. 2.
Figure 3B:
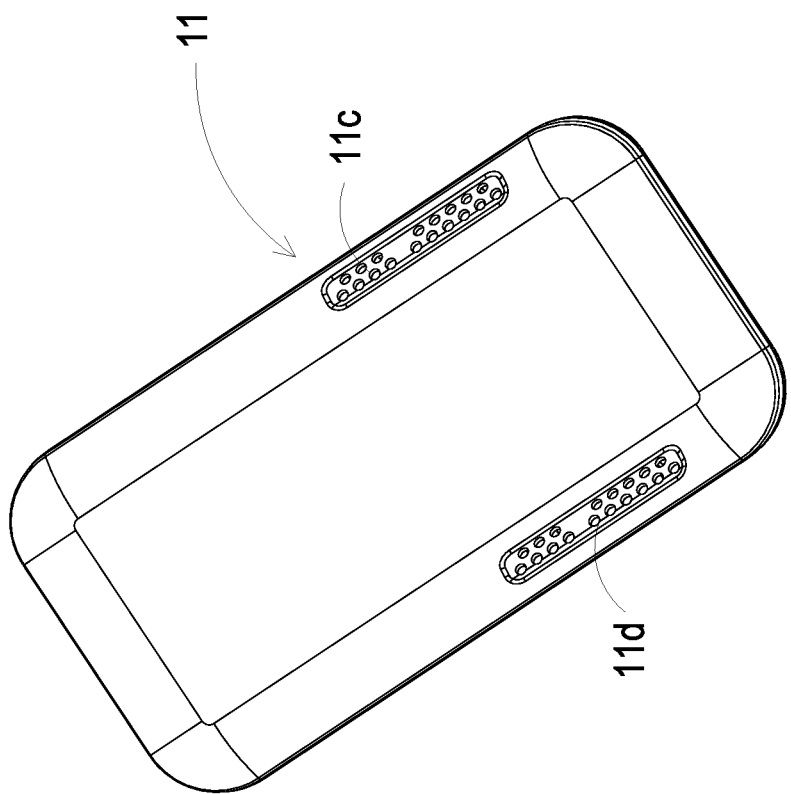
FIG. 3B is a schematic rear view illustrating the portable air quality monitoring device of FIG. 3A.
Figure 3C:
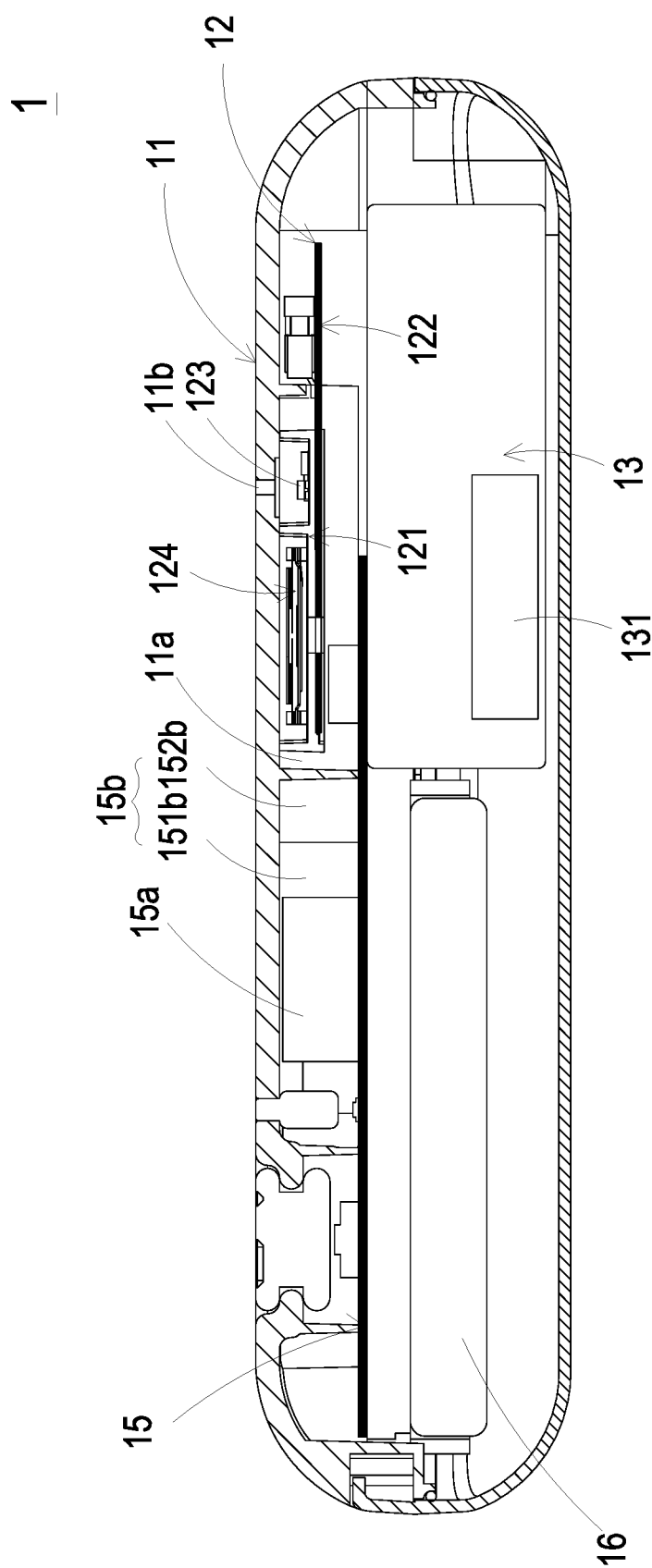
FIG. 3C is a schematic cross-sectional view illustrating the portable air quality monitoring device of FIG. 3A.
Figure 3D:
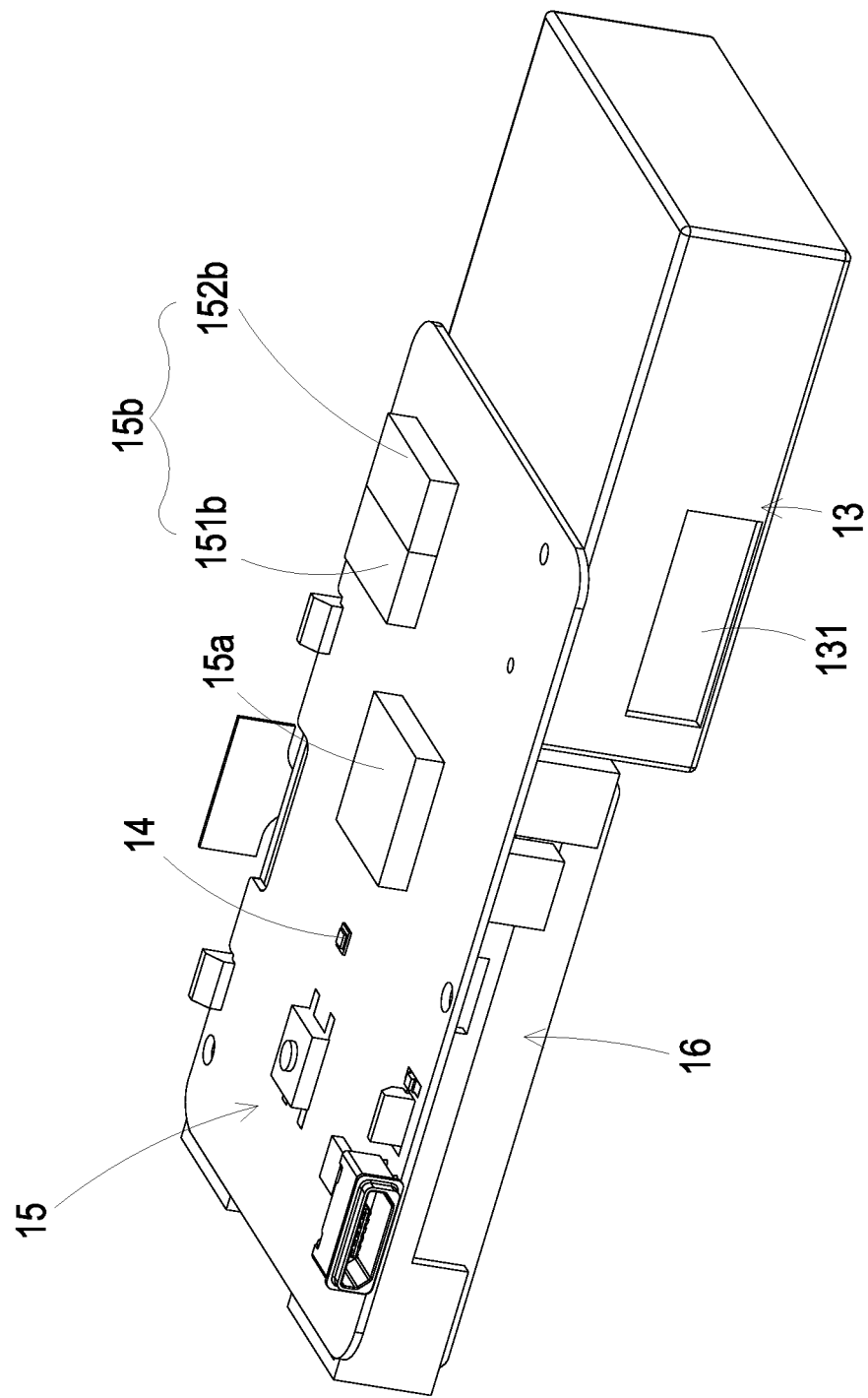
FIG. 3D is a schematic perspective view illustrating a part of an inner structure of the portable air quality monitoring device of FIG. 3A.

Please refer to FIGS. 2 to 3D. The portable air quality monitoring device 1 includes a main body 11, an air monitoring module 12, a particle detecting module 13, a GPS component 14 and a control module 15. The air monitoring module 12, the particle detecting module 13 and the control module 15 are disposed within the main body 11 to form a thin portable device. The main body 11 has a chamber 11a, a first inlet 11b, a second inlet 11c and an outlet 11d. The chamber 11a is disposed inside the main body 11 and communicates with the first inlet 11b, the second inlet 11c and the outlet 11d.

Please refer to FIGS. 2, 3C, and 4A to 4E. The air monitoring module 12 includes a compartment 121, a carrier 122, a gas sensor 123 and a gas actuator 124. The compartment 121 is disposed under the first inlet 11b, and is divided into a first chamber 121b and a second chamber 121c by the partition 121a. The partition 121a has a notch 121d for the communication between the first chamber 121b and the second chamber 121c. The first chamber 121b has an opening 121e. The second chamber 121c has an outlet aperture 121f. The compartment 121 further includes a receiving slot 121g disposed in the rear side for receiving the carrier 122. The carrier 122 is disposed and positioned within the receiving slot 121g so as to close the rear side of the compartment 121. The carrier 122 is assembled and sealed under the compartment 121 and is electrically coupled with the gas sensor 123. The gas sensor 123 penetrates the opening 121e so as to be disposed in the first chamber 121b. Consequently, the gas in the first chamber 121b is sensed by the gas sensor 123. The carrier 122 has a gas outlet aperture 122a disposed corresponding to the outlet aperture 121f. When the carrier 122 is assembled under the compartment 121, the gas outlet aperture 122a aligns with the outlet aperture 121f. The gas actuator 124 is disposed in the second chamber 121c so as to be separated from the gas sensor 123 disposed in the first chamber 121b. Namely, the heat generated by the actuation of the gas actuator 124 can be blocked by the partition 121a, so that the sensing result of the gas sensor 123 is not affected. The gas actuator 124 closes the bottom of the second chamber 121c, and is controlled to generate a guiding airflow. The gas is inhaled from the first inlet 11b of the main body 11, and sensed by the gas sensor 123. The gas is then transported to the second chamber 121c through the notch 121d. The gas passes through the gas actuator 124 and the outlet aperture 121f, and is discharged to the outside of the air monitoring module 12 through the gas outlet aperture 122a of the carrier 122. Finally, the gas is discharged out from the outlet 11d of the main body 11.

Figure 5A:
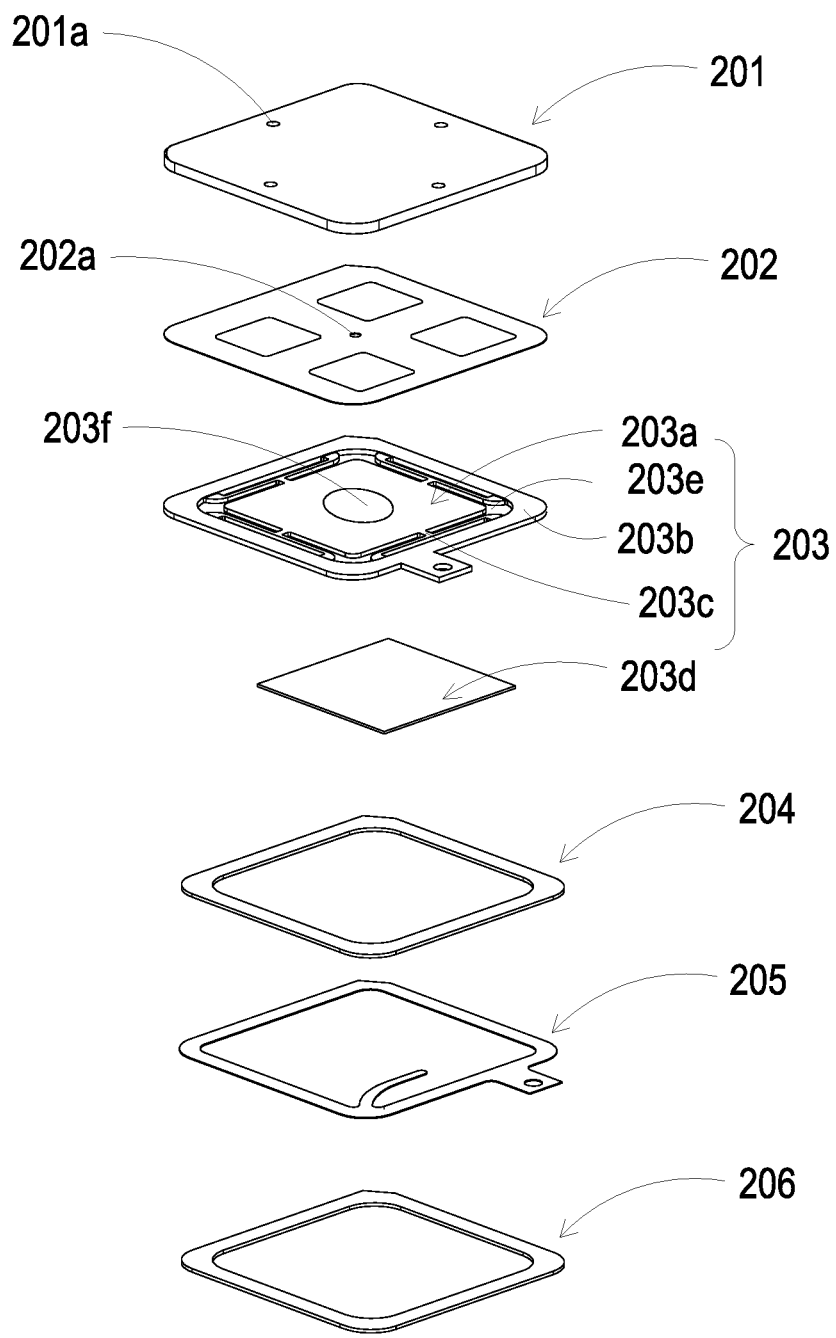
FIG. 5A is a schematic exploded view illustrating a miniature pump used in the air monitoring module of the portable air quality monitoring device of the present disclosure.
Figure 5B:
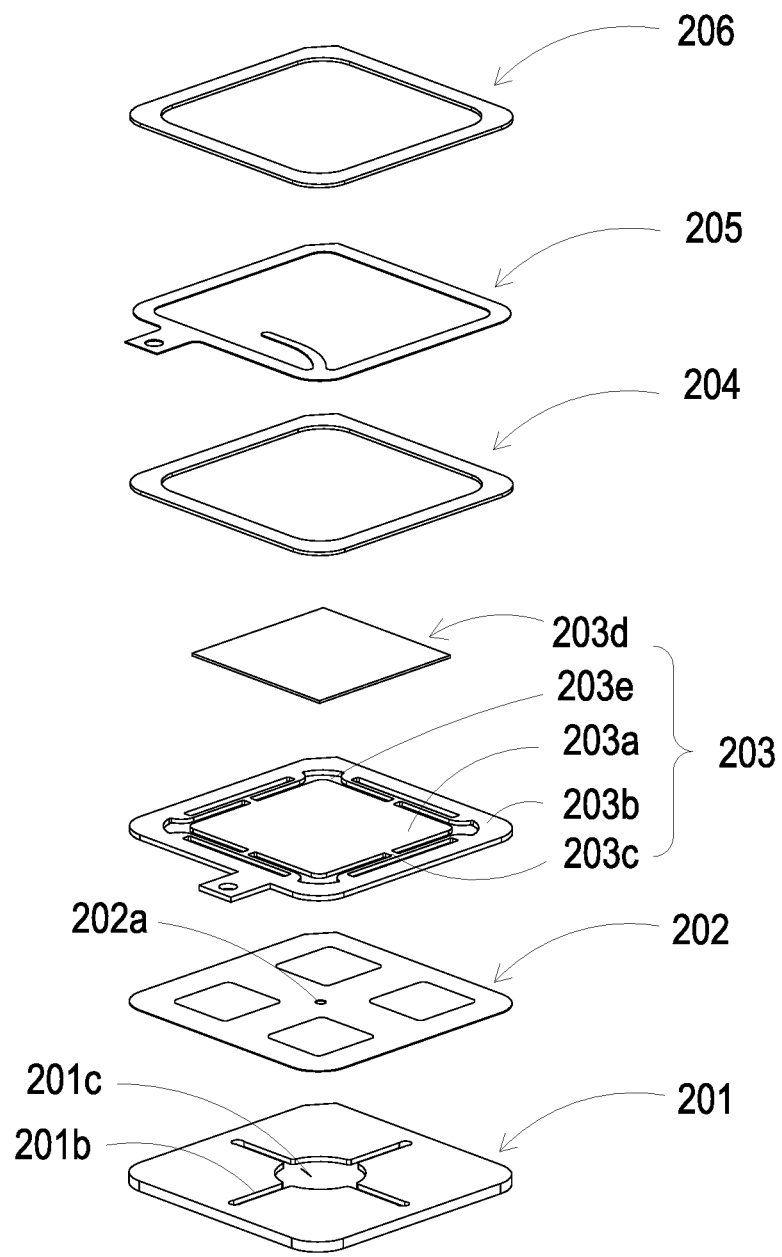
FIG. 5B is a schematic exploded view illustrating the miniature pump of FIG. 5A and taken along another viewpoint.

Please refer to FIGS. 5A and 5B. In an embodiment, the gas actuator 124 is a miniature pump 20. The miniature pump 20 includes a fluid inlet plate 201, a resonance plate 202, a piezoelectric actuator 203, a first insulation plate 204, a conducting plate 205 and a second insulation plate 206. The fluid inlet plate 201, the resonance plate 202, the piezoelectric actuator 203, the first insulation plate 204, the conducting plate 205 and the second insulation plate 206 are stacked on each other sequentially. The fluid inlet plate 201 has at least one fluid inlet hole 201a, at least one convergence channel 201b, and a convergence chamber 201c. The at least one fluid inlet hole 201a is disposed for introducing the fluid. The at least one convergence channel 201b communicates with the convergence chamber 201c. The at least one convergence channel 201b is disposed corresponding in position to the fluid inlet hole 201a for guiding the fluid from the fluid inlet hole 201a toward the convergence chamber 201c. In this embodiment, the number of the at least one fluid inlet hole 201a and the number of the at least one convergence channel 201b are the same, and the fluid inlet plate 201 has 4 fluid inlet holes 201a and 4 convergence channels 201b, but not limited thereto.

Figure 6A:
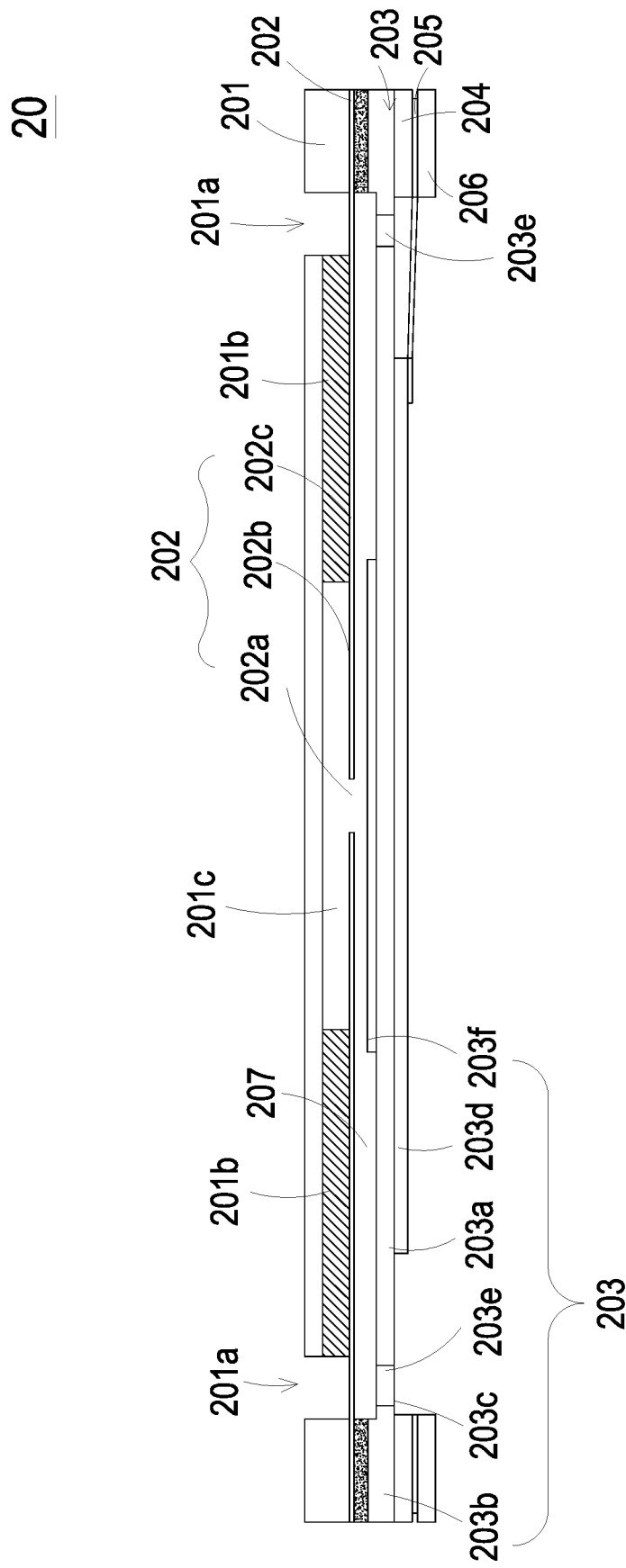
FIG. 6A is a schematic cross-sectional view illustrating the miniature pump of FIG. 5A.

Please refer to FIGS. 5A, 5B and 6A. In this embodiment, the resonance plate 202 is attached on the fluid inlet plate 201, and has a central aperture 202a, a movable part 202b and a fixed part 202c. The central aperture 202a is disposed at the center of the resonance plate 202, and is corresponding in position to the convergence chamber 201c of the fluid inlet plate 201. The movable part 202b surrounds the central aperture 202a and corresponds in position to the convergence chamber 201c. The fixed part 202c surrounds the movable part 202b and is fixedly attached on the fluid inlet plate 201.

The piezoelectric actuator 203 comprises a suspension plate 203a, an outer frame 203b, at least one bracket 203c, a piezoelectric plate 203d, at least one vacant space 203e and a bulge 203f. The suspension plate 203a is square-shaped because the square suspension plate 203a is more power-saving than the circular suspension plate. Generally, the consumed power of the capacitive load at the resonance frequency is positively related to the resonance frequency. Since the resonance frequency of the square suspension plate 203a is obviously lower than that of the circular square suspension plate, the consumed power of the square suspension plate 203a is fewer. Therefore, the square suspension plate 203a in this embodiment has the effectiveness of power-saving. The outer frame 203b surrounds an outer side of the suspension plate 203a. At least one bracket 203c is connected between the suspension plate 203a and the outer frame 203b for providing an elastic support for the suspension plate 203a. The piezoelectric plate 203d has a side, and a length of the side of the piezoelectric plate 203d is less than or equal to that of the suspension plate 203a. The piezoelectric plate 203d is attached on a surface of the suspension plate 203a, and when a voltage is applied to the piezoelectric plate 203d, the suspension plate 203a is driven to undergo a bending vibration. The suspension plate 203a, the outer frame 203b and the at least one bracket 203c corporately form the at least one vacant space 203e, and the at least one vacant space 203e is disposed for allowing the fluid to pass through. The bulge 203f is disposed on another surface of the suspension plate 203a that is opposite to the piezoelectric plate 203d. In this embodiment, the bulge 203f and the suspension plate 203a are integrally formed from one piece by an etching process, and the bulge 203f is a protruding structure on another surface of the suspension plate 203a opposite to the piezoelectric plate 203d.

Please refer to FIGS. 5A, 5B and 6A again. In this embodiment, a chamber space 207 is formed between the suspension plate 203a and the resonance plate 202, and the chamber space 207 can be formed by filling a gap between the resonance plate 202 and the outer frame 203b of the piezoelectric actuator 203 with a material, such as a conductive adhesive, but not limited thereto. Thus, a specific depth between the resonance plate 202 and the suspension plate 203a is maintained to allow the fluid to pass rapidly. In addition, since the resonance plate 202 and the suspension plate 203a are maintained at a suitable distance, so that the contact interference therebetween is reduced and the generated noise is largely reduced. In some other embodiments, the thickness of the conductive adhesive filled into the gap between the resonance plate 202 and the outer frame 203b of the piezoelectric actuator 203 is reduced by increasing the height of the outer frame 203b of the piezoelectric actuator 203. In that, the suspension plate 203a and the resonance plate 202 are maintained at a suitable distance and the thickness of conductive adhesive filled in the miniature pump 20 is not influenced due to the hot pressing temperature and the cooling temperature. It avoids that the actual size of the chamber space 207 is influenced due to the thermal expansion and contraction after the entire miniature pump 20 is assembled. In addition, the size of the chamber space 207 will affect the effectiveness of the miniature pump 20, so therefore it is important to maintain the size of the chamber space 207.

Figure 6B:
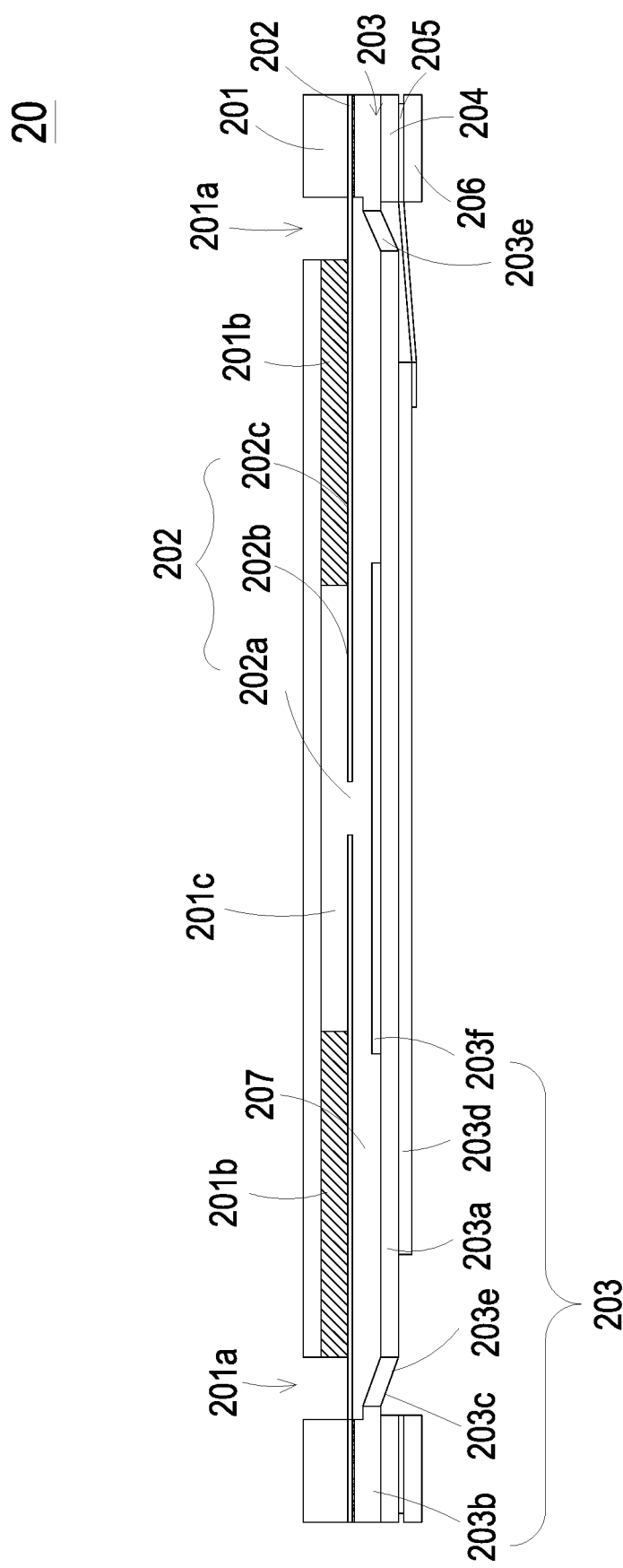
FIG. 6B is a schematic cross-sectional view illustrating the miniature pump of FIG. 5A and taken along another viewpoint.

Please refer to FIG. 6B, in some other embodiments, the suspension plate 203a is formed by stamping to make it extend at a distance in a direction away from the resonance plate 202. The extended distance can be adjusted through the at least one bracket 203c formed between the suspension plate 203a and the outer frame 203b. Consequently, the top surface of the bulge 203f disposed on the suspension plate 203a and the coupling surface of the outer frame 203b are non-coplanar. That is, top surface of the bulge 203f is lower than the coupling surface of the outer frame 203b. By utilizing a small amount of filling materials, such as a conductive adhesive applied to the coupling surface of the outer frame 203b, the piezoelectric actuator 203 is attached to the fixed part 202c of the resonance plate 202 by hot pressing, thereby assembling the piezoelectric actuator 203 and the resonance plate 202 in combination. Thus, the structure of the chamber space 207 is improved by directly stamping the suspension plate 203a of the piezoelectric actuator 203 described above. In this way, the required chamber space 207 can be achieved by adjusting the stamping distance of the suspension plate 203a of the piezoelectric actuator 203. It benefits from simplifying the structural design of the chamber space 207, and also achieves the advantages of simplifying the process and shortening the processing time. In addition, the first insulation plate 204, the conducting plate 205 and the second insulation plate 206 are all thin frame-shaped sheets, but are not limited thereto, and are sequentially stacked on the piezoelectric actuator 203 to form the entire structure of the miniature pump 20.

Figure 6C:
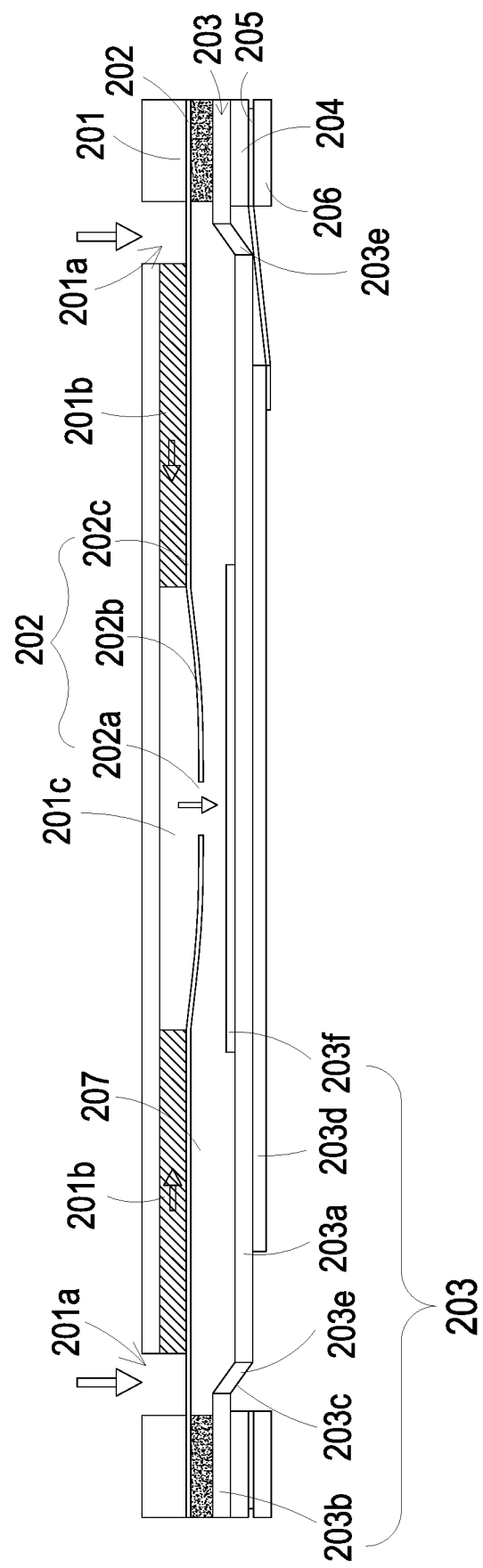
FIGS. 6C to 6E schematically illustrate the actions of the fluid actuating device of the miniature pump of 6A.
Figure 6D:
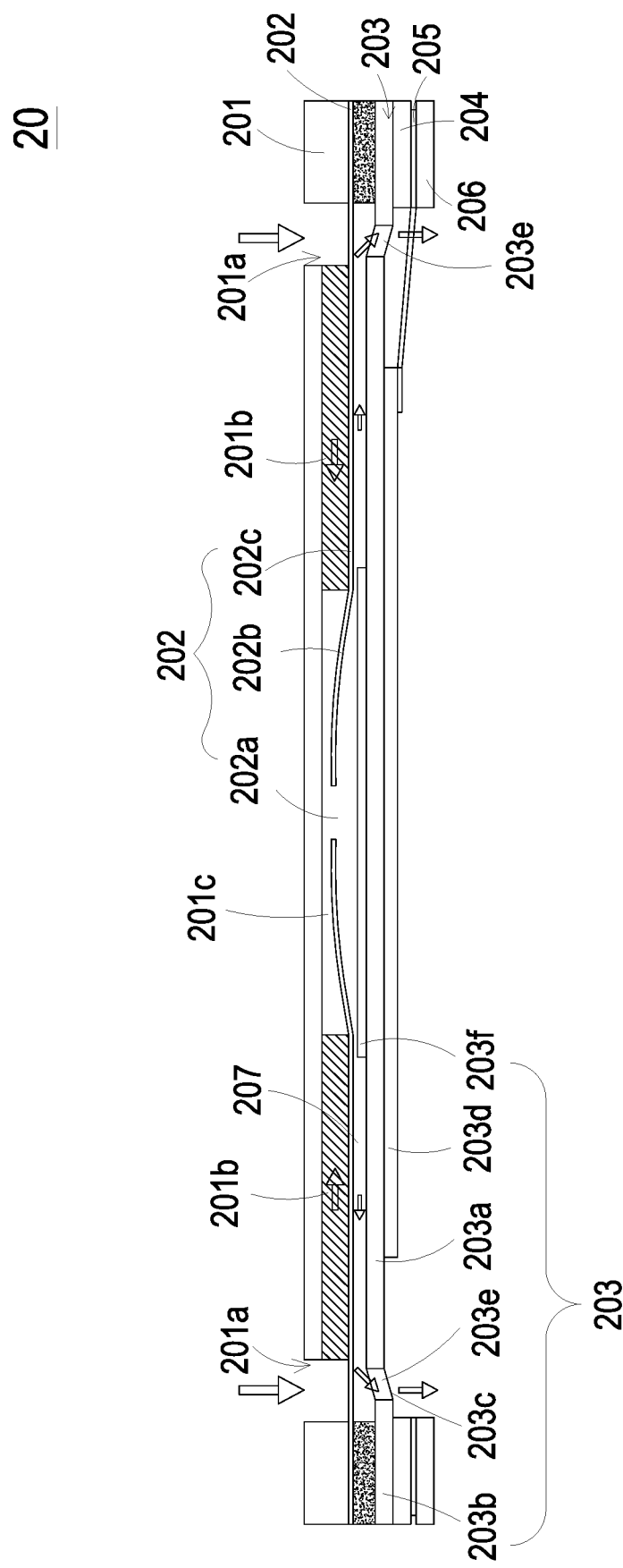
Figure 6E:
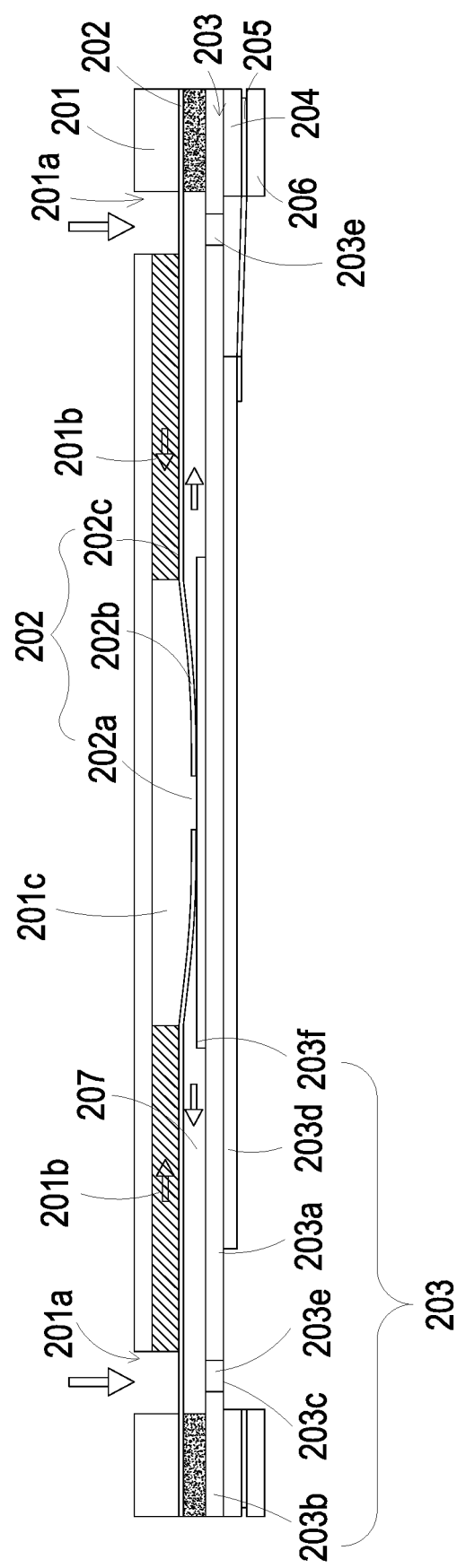

In order to understand the actuations of the miniature pump 20, please refer to FIG. 6C to FIG. 6E. Please refer to FIG. 6C, when the piezoelectric plate 203d of the piezoelectric actuator 203 is deformed in response to an applied voltage, the suspension plate 203a is driven to displace in the direction away from the resonance plate 202. In that, the volume of the chamber space 207 is increased, a negative pressure is formed in the chamber space 207, and the fluid in the convergence chamber 201c is introduced into the chamber space 207. At the same time, the resonance plate 202 is in resonance and is thus displaced synchronously. Thereby, the volume of the convergence chamber 201c is increased. Since the fluid in the convergence chamber 201c is introduced into the chamber space 207, the convergence chamber 201c is also in a negative pressure state, and the fluid is sucked into the convergence chamber 201c through the fluid inlet holes 201a and the convergence channels 201b.

Then, as shown in FIG. 6D, the piezoelectric plate 203d drives the suspension plate 203a to displace toward the resonance plate 202 to compress the chamber space 207. Similarly, the resonance plate 202 is actuated in resonance to the suspension plate 203a and is displaced. Thus, the fluid in the chamber space 207 is further transmitted to pass through the vacant spaces 203e and it achieves the effectiveness of fluid transmission.

Finally, as shown in FIG. 6E, when the suspension plate 203a is driven to return to an initial state, the resonance plate 202 is also driven to displace. In that, the resonance plate 202 pushes the fluid in the chamber space 207 toward the vacant spaces 203e, and the volume of the convergence chamber 201c is increased. Consequently, the fluid can continuously pass through the fluid inlet holes 201a and the convergence channels 231b, and can be converged in the convergence chamber 201c. By repeating the actuations illustrated in FIGS. 6C to 6E continuously, the miniature pump 20 can continuously transmit the fluid at high speed. It achieves the transmitting and outputting operations of the miniature pump 20.

Please refer to FIG. 6A, the fluid inlet plate 201, the resonance plate 202, the piezoelectric actuator 203, the first insulation plate 204, the conducting plate 205 and the second insulation plate 206 of the miniature pump 20 can be manufactured by a surface micromachining process of a micro-electromechanical-systems (MEMS). In such a manner, the volume of each of the miniature pump 20 can be decreased so as to form a MEMS gas pump.

Figure 4A:
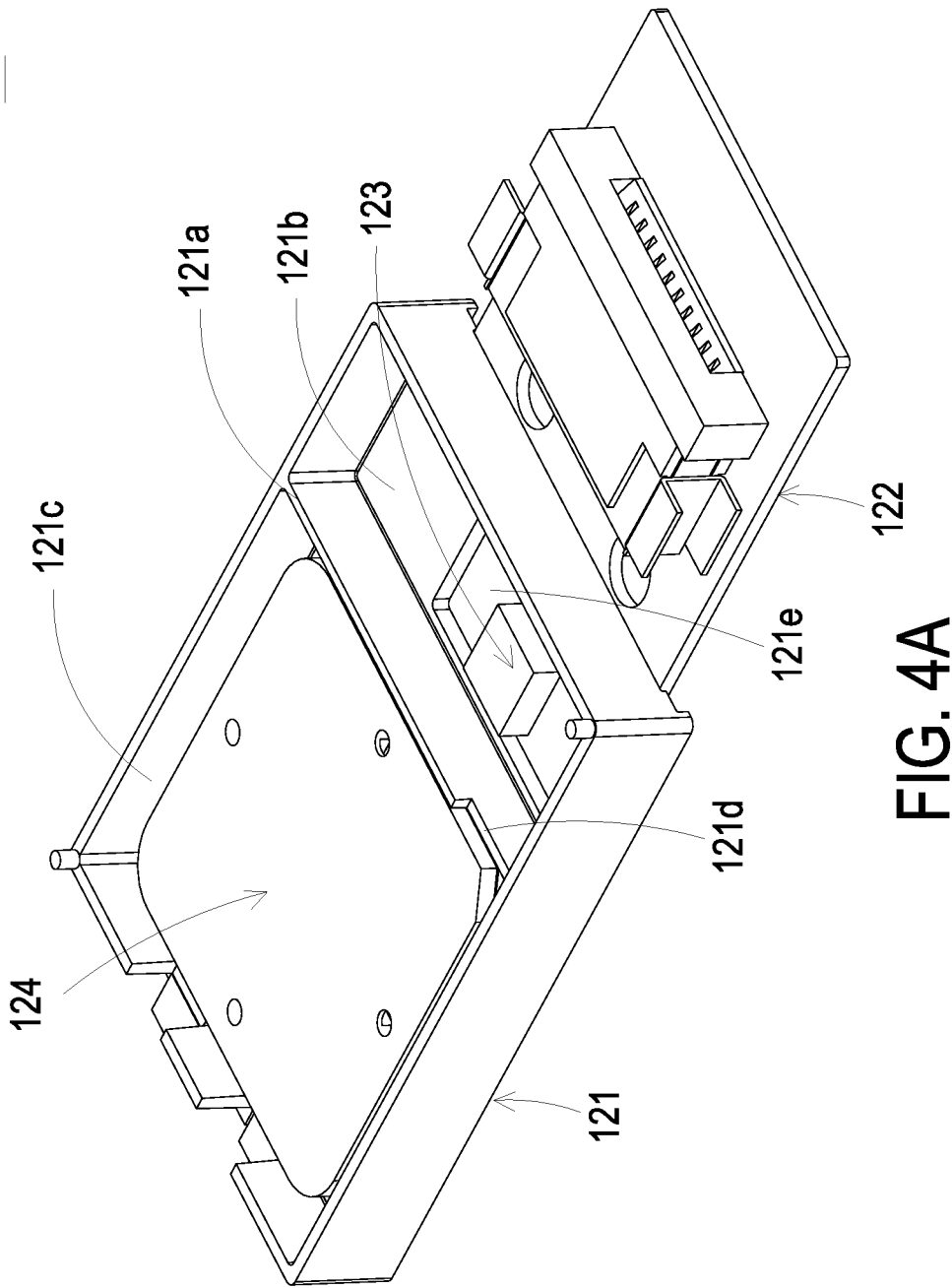
FIG. 4A is a schematic perspective view illustrating an air monitoring module of the portable air quality monitoring device of FIG. 3A.
Figure 4B:
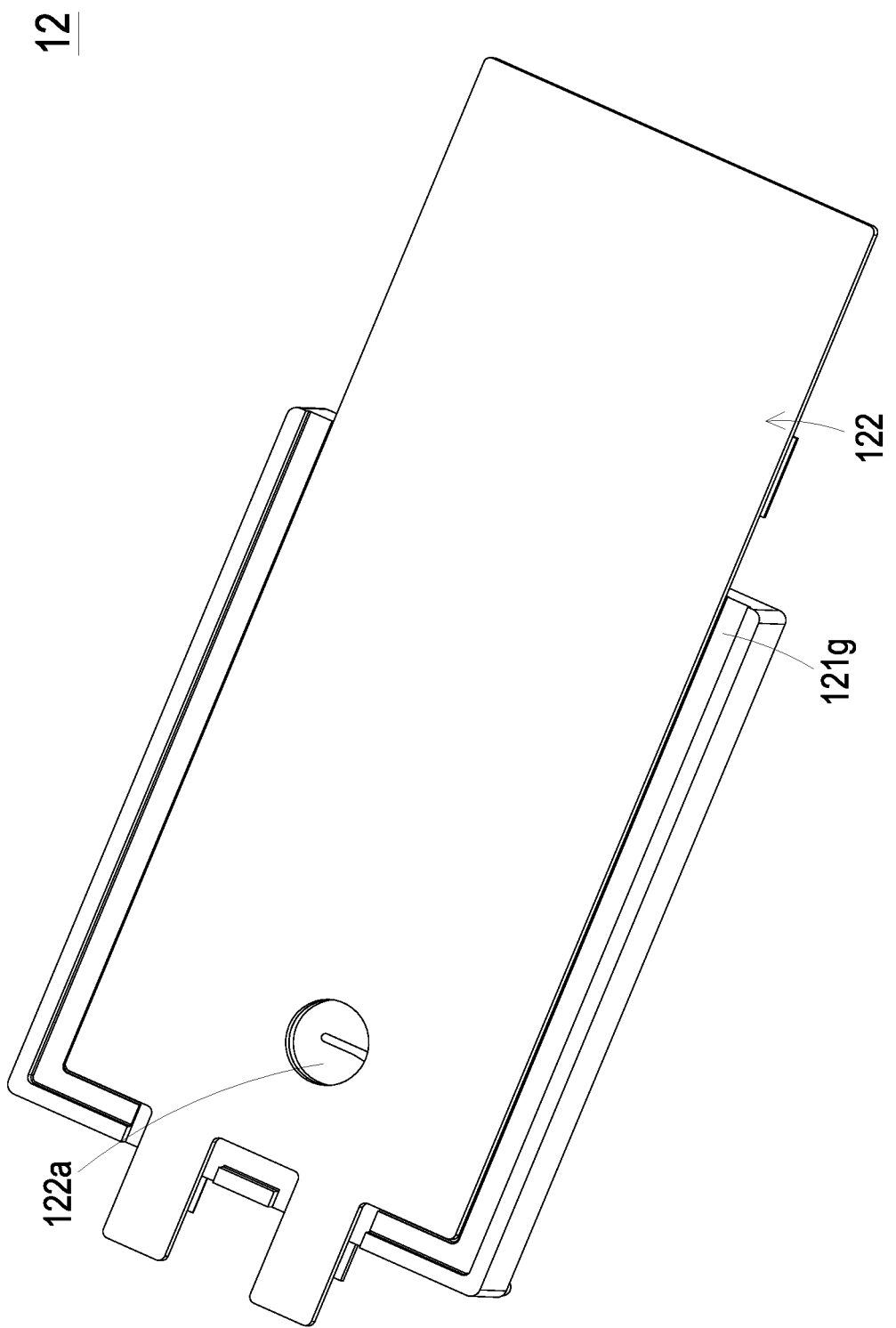
FIG. 4B is a schematic rear view illustrating the air monitoring module of the portable air quality monitoring device of FIG. 4A.
Figure 4C:
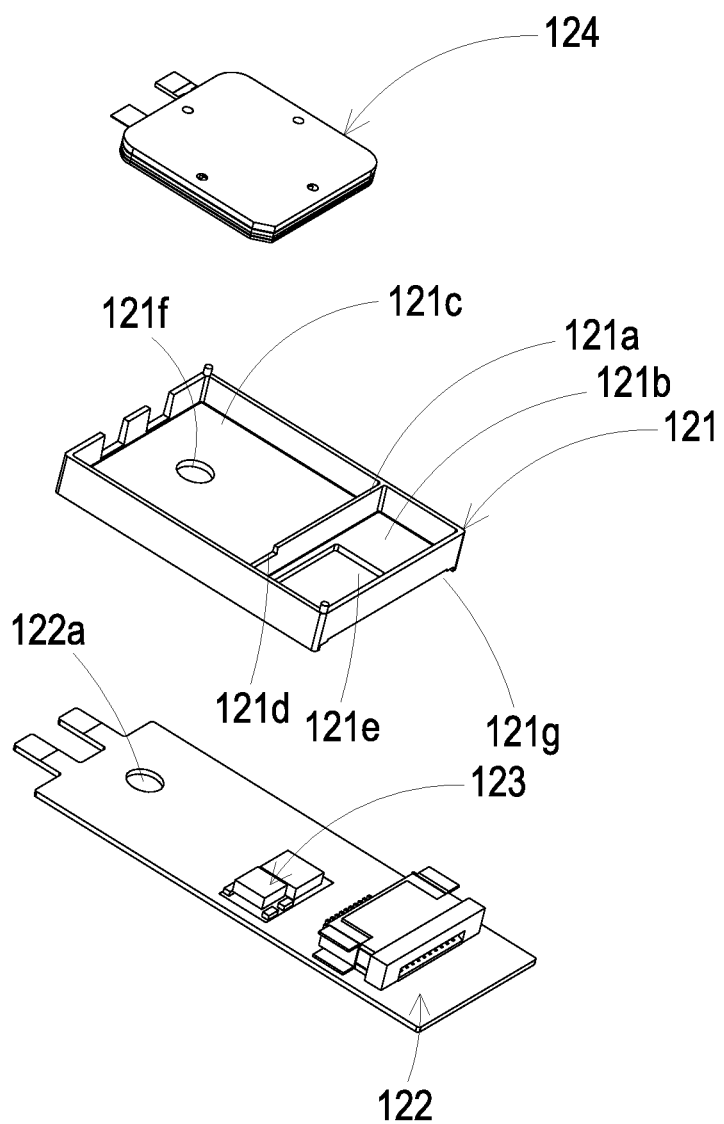
FIG. 4C is a schematic exploded view illustrating the air monitoring module of the portable air quality monitoring device of FIG. 4A.
Figure 4D:
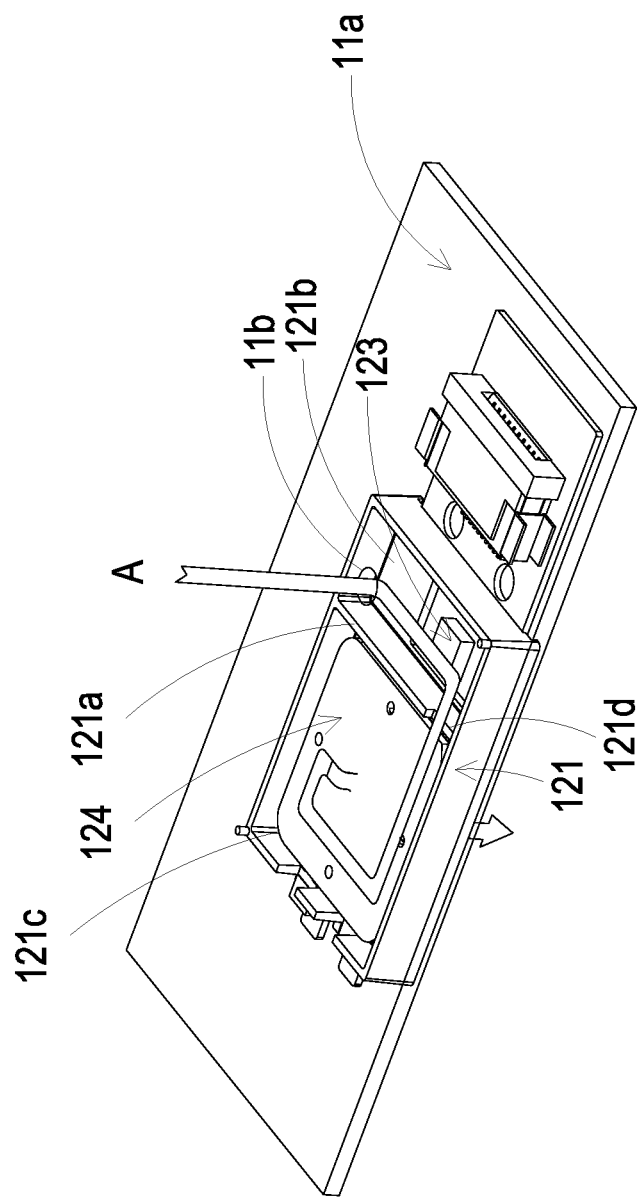
FIG. 4D is a schematic view illustrating the air flow directions of the monitoring module of the portable air quality monitoring device of FIG. 4A.
Figure 4E:
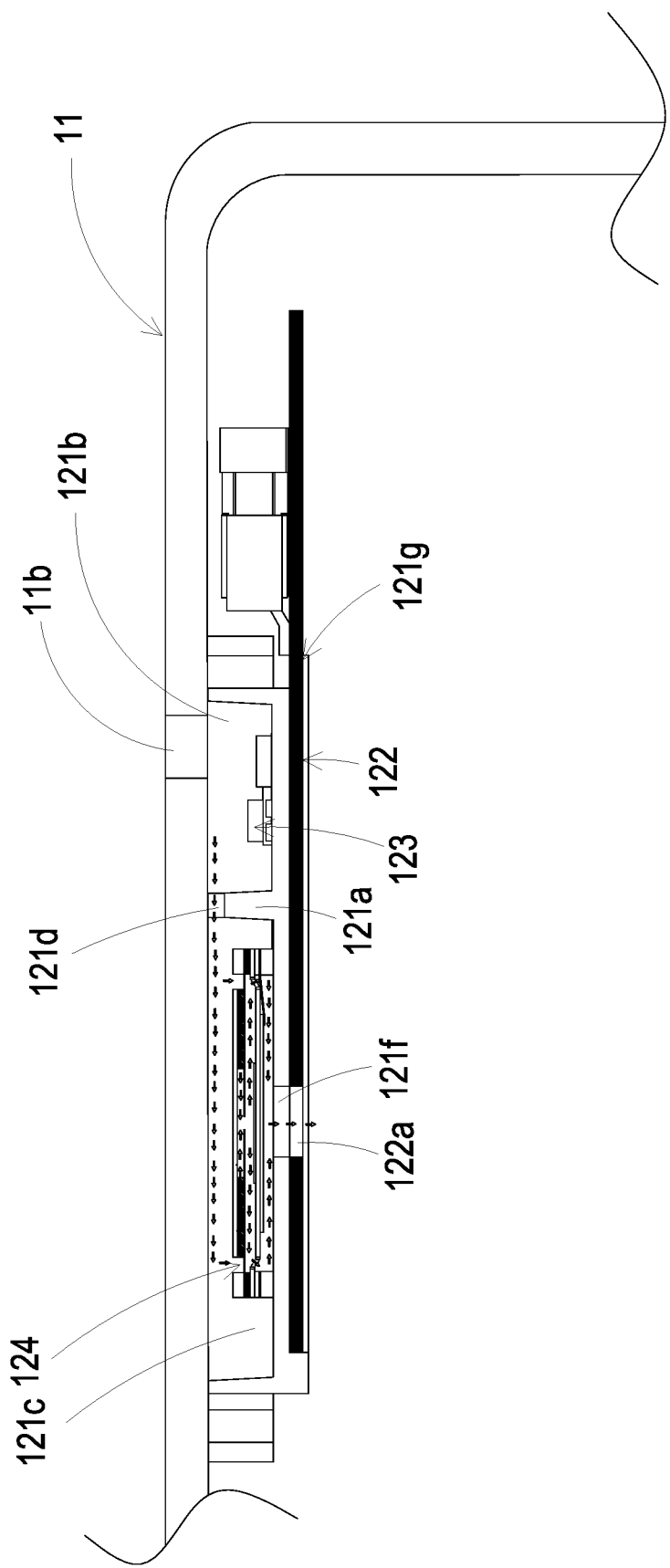
FIG. 4E is a schematic cross-sectional view illustrating the air flow directions of the monitoring module of the portable air quality monitoring device of FIG. 4A.

Please refer to FIG. 4D and FIG. 4E again. For clearly illustrating the airflow direction of the air monitoring module 12, the main body 11 of FIG. 4D is ignored herein. In the embodiment, when the air monitoring module 12 mounts in the chamber 11a of the main body 11, the first inlet 11b is in corresponding to the first chamber 121b of the compartment 121. In addition, the first inlet 11b of the main body 11 is not in corresponding to the gas sensor 123 disposed in the first chamber 121b. Namely, the first inlet 11b is not disposed right on the top of the gas sensor 123, both of which are misaligned with each other. In this embodiment, when the gas actuator 124 is driven, a negative pressure is generated in the second chamber 121c. Consequently, the gas is inhaled from the exterior of the main body 11 into the first chamber 121b, and is sensed by the gas sensor 123 disposed in the first chamber 121b, so that an air quality information is acquired. As the gas actuator 124 is continuously driven, the sensed gas is continuously guided into the second chamber 121c by passing through the notch 121d of the partition 121a, and then is discharged to the outside of the compartment 121 via the outlet aperture 121f and the gas outlet aperture 122a of the carrier 122. Consequently, the guiding airflow path with a single direction for monitoring is constructed (as shown in the arrow A of FIG. 4A).

An example of the gas sensor 123 includes but is not limited to an oxygen sensor, a carbon monoxide sensor, a carbon dioxide sensor, or the combination thereof. In some embodiments, the gas sensor 123 includes a temperature sensor, a humidity sensor, or both of them. In some other embodiments, the gas sensor 123 includes a volatile organic compound sensor. Alternatively, the gas sensor 123 includes but is not limited to a bacterial sensor, a virus sensor, a microbiological sensor or the combination thereof.

As described above, the portable air quality monitoring device 1 can monitor the ambient air quality at any time by utilizing the air monitoring module 12. Meanwhile, due to the gas actuator 124 can inhale gas rapidly and constantly into the air monitoring module 12, the sensing efficiency of the gas sensor 123 is increased. In addition, the gas sensor 123 and the gas actuator 124 are apart from each other in correspondence to the separation design of the first chamber 121b and second chamber 121c. Consequently, the monitoring accuracy of the gas sensor 123 would not be influenced by the heat generated from the actuation of the gas actuator 124 or other components. Consequently, the air quality notification device of the present disclosure is capable of monitoring the air quality everywhere and at any time and increasing the monitoring accuracy.

Figure 7:
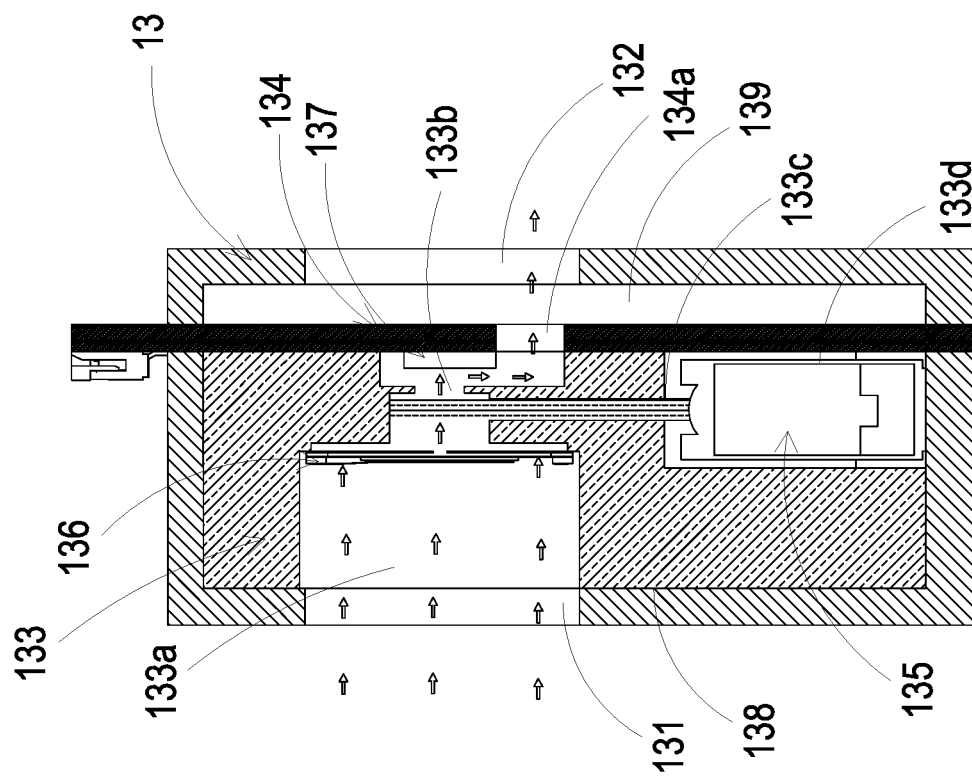
FIG. 7 is a schematic cross-sectional view illustrating a particle detecting module used in the portable air quality monitoring device of the present disclosure.
Figure 8:
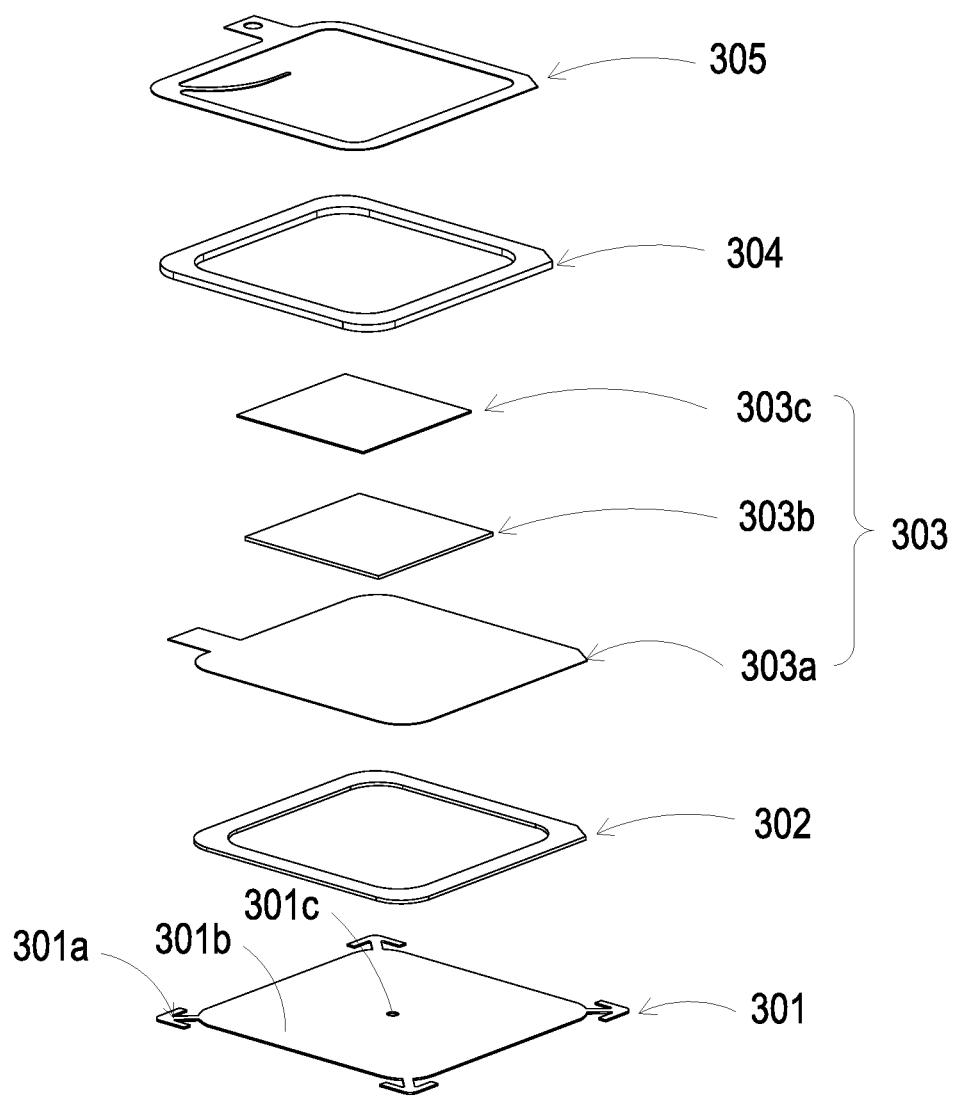
FIG. 8 is a schematic exploded view illustrating a blast miniature pump used in the portable air quality monitoring device of the present disclosure.

Please refer to FIG. 3C, FIG. 3D and FIG. 7. In the embodiment, the portable air quality monitoring device 1 further includes a particle detecting module 13 for monitoring the particle of the air. The particle detecting module 13 is disposed in the chamber 11a of the main body 11. The particle detecting module 13 includes a gas inlet hole 131, a gas outlet hole 132, a fine particle detecting base 133, a carrying partition 134, a laser emitter 135, a fine particle actuator 136 and a fine particle sensor 137. The gas inlet hole 131 is in corresponding to the second inlet 11c of the main body, and the gas outlet hole 132 is in corresponding to the outlet 11d of the main body, by which the gas is inhaled within the particle detecting module 13 from the gas inlet hole 131 and exhausted by the gas outlet hole 132. The fine particle detecting base 133 and the carrying partition 134 are disposed in the particle detecting module 13, so that a first fine particle chamber 138 and a second fine particle chamber 139 are defined by the carrying partition 134. There is a communication opening 134a disposed on the carrying partition 134 for being in communication between the first fine particle chamber 138 and the second fine particle chamber 139. In this embodiment, the fine particle detecting base 133 is disposed in the first fine particle chamber 138 and adjacent to the carrying partition 134. The fine particle detecting base 133 includes a receiving slot 133a, a detecting channel 133b, a light-beam channel 133c and a receiving chamber 133d. The receiving slot 133a is exactly aligned with the gas inlet hole 131. The detecting channel 133b is in communication between the receiving slot 133a and the communication opening 134a of the carrying partition 134. The receiving chamber 133d is disposed at one side of the detecting channel 133b, and the light-beam channel 133c is in communication between the receiving chamber 133d and the detecting channel 133b. In the embodiment, the light-beam channel 133c is disposed across the detecting channel 133b. That is, the light-beam channel 133c is perpendicular to the detecting channel 133b, and the light-beam channel 133c and the detecting channel 133b intersect with each other. Consequently, the gas inlet hole 131, the receiving slot 133a, the detecting channel 133b, the communication opening 134a, the second fine particle chamber 139 and the gas outlet hole 132 of the particle detecting module 13 integrally forms a gas passage for guiding gas flowing in a single direction (as shown in the arrows of FIG. 7).

As mentioned above, the laser emitter 135 is disposed in the receiving chamber 133d, and the fine particle actuator 136 is disposed in the receiving slot 133a. The fine particle sensor 137 is electrically connected to the carrying partition 134 and is in communication with the detecting channel 133b, to emit a light beam into the light-beam channel 133c. The light-beam channel 133c is in communication with the detecting channel 133b to allow the light beam emitted from the laser emitter 135 to irradiate an inner space of the detecting channel 133b. When the air within the detecting channel 133b is irradiated by the light beam, the suspended particles contained in the air are irradiated to generate scattering light spots projected on the fine particle sensor 137. The fine particle sensor 137 receives the scattering light sports generated by the suspended particles and measures the sizes and concentrations of the suspended particles. The fine particle sensor 137 may be a light detecting sensor or a PM 2.5 sensor.

In the embodiment, the detecting channel 133b of the particle detecting module 13 is vertically in correspondence to the gas inlet hole 131, so that the gas can be directly introduced into the detecting channel 133b. In addition, since the fine particle actuator 136 is disposed in the receiving slot 133a, the gas introducing rate is increased. Consequently, the gas can be introduced into the detecting channel 133b faster, so that the sensing efficiency of the fine particle actuator 136 is enhanced.

The above description illustrates the features of the particle detecting module 13 of the present disclosure. In this embodiment, the fine particle actuator 136 can also be a miniature pump 20, but not limited thereto. The structures and operations of the miniature pump 20 are same as described above, and will not be described herein.

In some embodiments, the gas actuator 124 and the fine particle actuator 136 can be miniature pumps 20. In some other embodiments, the gas actuator 124 and the fine particle actuator 136 can also be a blast miniature pump 30, respectively. Please refer to FIG. 8 and FIGS. 9A to 9C. The blast miniature pump 30 includes a nozzle plate 301, a chamber frame 302, an actuating body 303, an insulation frame 304 and a conducting frame 305 stacked on each other sequentially. The nozzle plate 301 includes a plurality of brackets 301a, a suspension plate 301b and a central aperture 301c. The suspension plate 301b is permitted to undergo a bending vibration. The pluralities of brackets 301a are connected to the periphery of the suspension plate 301b. In the embodiment, there are four brackets 301a, which are connected to four corners of the suspension plate 301b, respectively, but the present disclosure is not limited thereto. The central aperture 301c is formed at a central position of the suspension plate 301b. The chamber frame 302 is stacked on the suspension plate 301b. The actuating body 303 is stacked on the chamber frame 302. The actuating body 303 includes a piezoelectric carrying plate 303a, an adjusting resonance plate 303b and a piezoelectric plate 303c. The piezoelectric carrying plate 303a is stacked on the chamber frame 302. The adjusting resonance plate 303b is stacked on the piezoelectric carrying plate 303a. The piezoelectric plate 303c is stacked on the adjusting resonance plate 303b. The piezoelectric plate 303c is configured to drive the piezoelectric carrying plate 303a and the adjusting resonance plate 303b to bend and vibrate in the reciprocating manner in response to the applied voltage and the deformation thereof. The insulation frame 304 is stacked on the piezoelectric carrying plate 303a of the actuating body 303. The conducting frame 305 is stacked on the insulation frame 304. A resonance chamber 306 is formed among the actuating body 303, the chamber frame 302 and the suspension plate 301b.

Figure 9A:
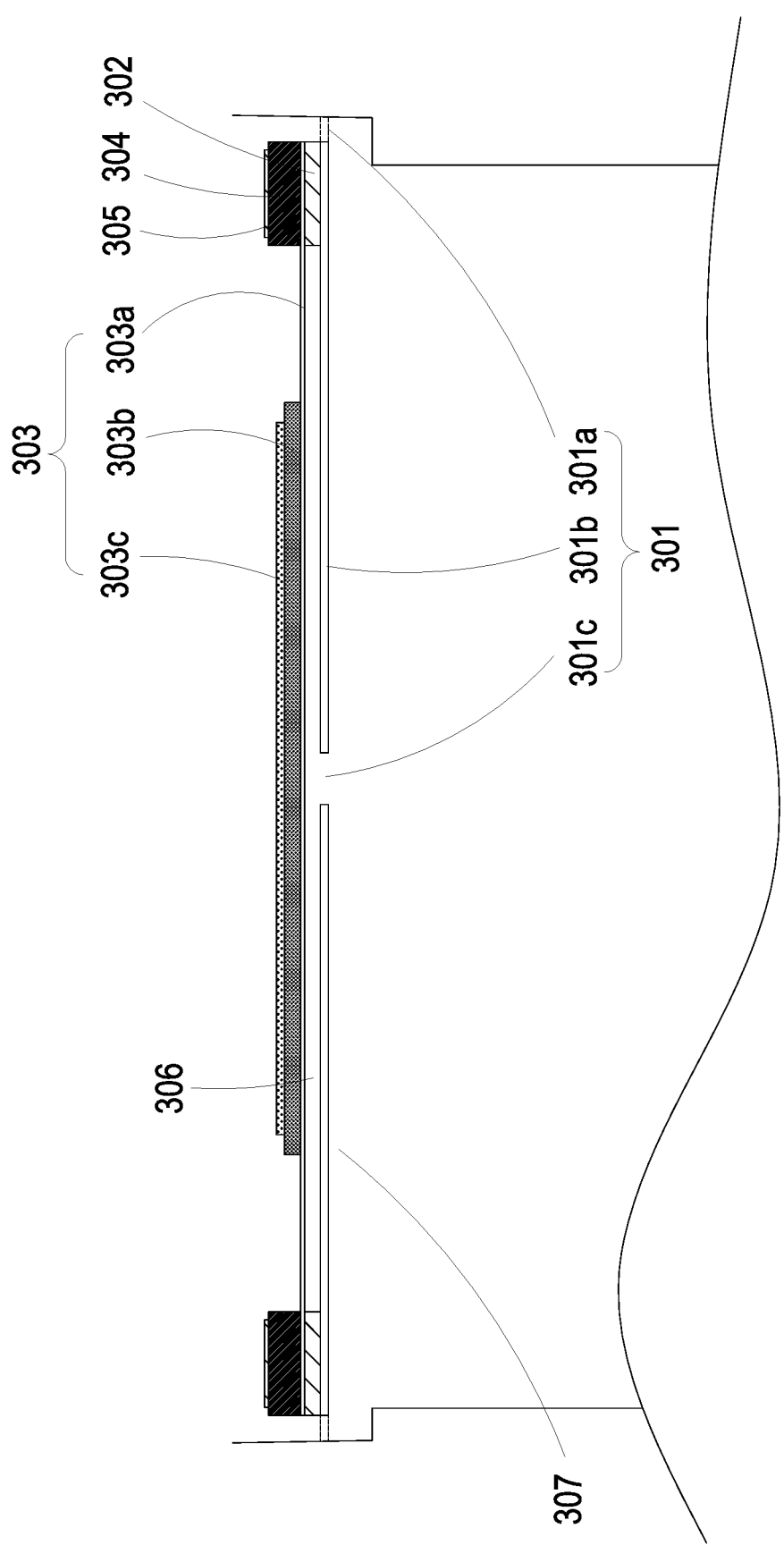
FIGS. 9A to 9C schematically illustrate the actions of the blast miniature pump of FIG. 8.
Figure 9B:
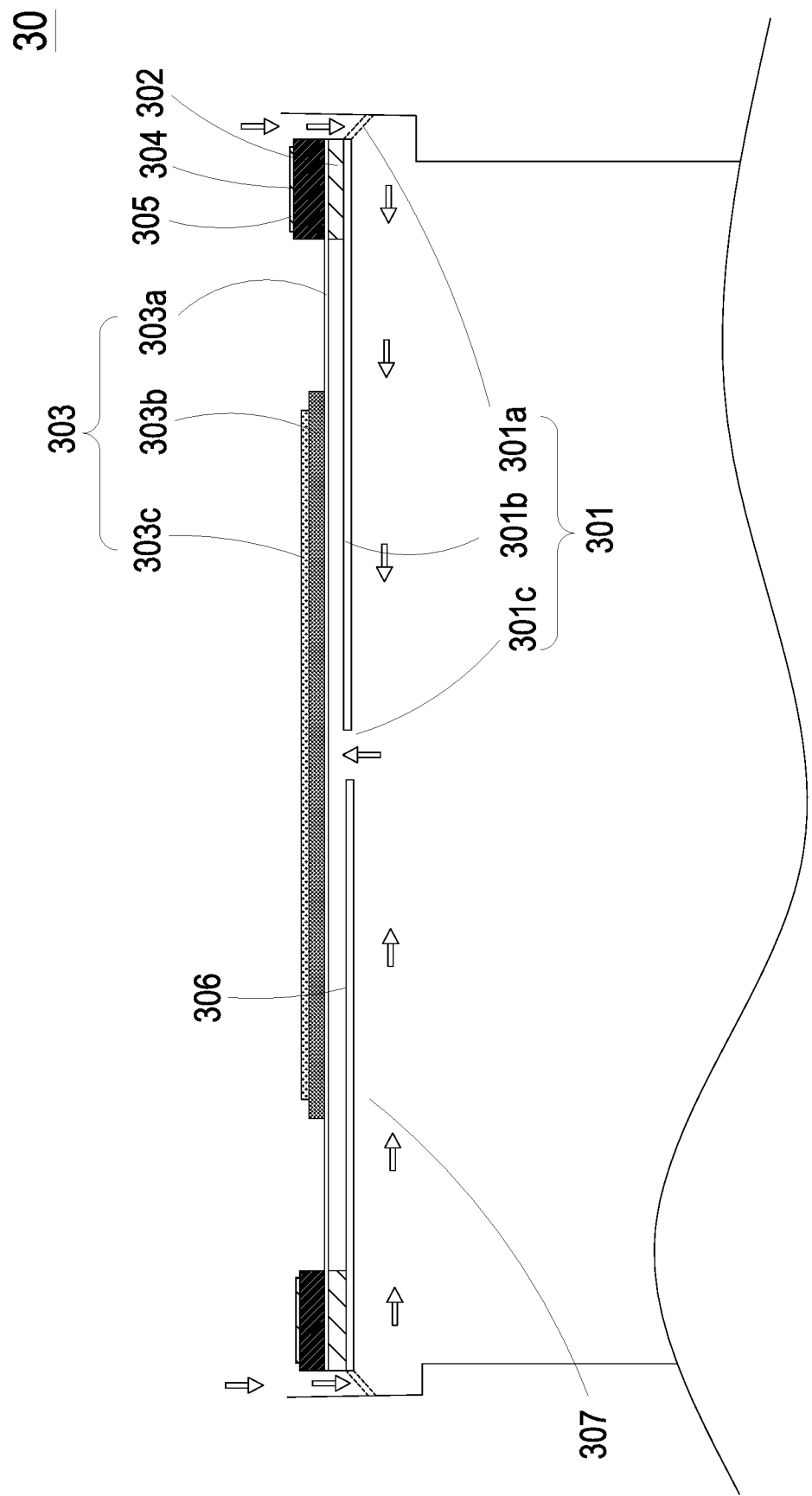
Figure 9C:
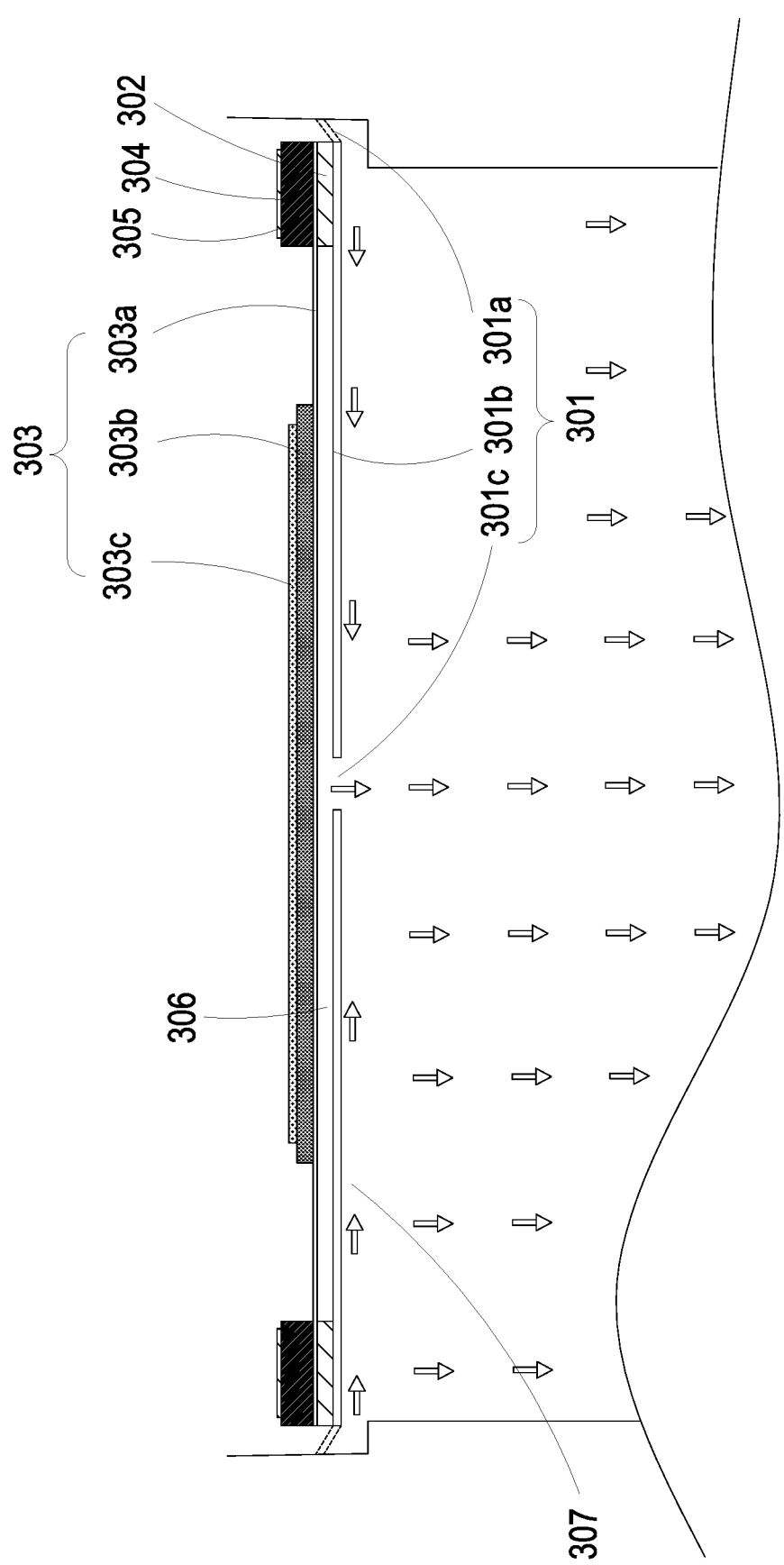

Please refer to FIGS. 9A to 9C. FIGS. 9A to 9C schematically illustrate the actions of the blast miniature pump of FIG. 8. Please refer to FIG. 8 and FIG. 9A firstly. The blast miniature pump 30 is fixedly disposed by the plurality of brackets 301a, and an airflow chamber 307 is formed under the bottom of the nozzle plate 301. Please refer to FIG. 9B again. When the piezoelectric plate 303c of the actuating body 303 is actuated by an applied voltage, the piezoelectric plate 303c of the actuating body 303 is deformed owing to the piezoelectric effect, and the adjusting resonance plate 303b and the piezoelectric carrying plate 303a are simultaneously driven to vibrate. Thereby, the nozzle plate 301 is driven to move due to the Helmholtz resonance effect, and the actuating body 303 is displaced upwardly. As so, the volume of the airflow chamber 307 is expanded, and a negative pressure is formed in the airflow chamber 307. The gas outside the blast miniature pump 30 is transported into the airflow chamber 307 through the vacant spaces formed among the suspension plate 301b and the brackets 301a of the nozzle plate 301 due to the pressure gradient, whereby the airflow chamber 307 is pressurized. Finally, please refer to FIG. 9C. The gas continuously flows into the airflow chamber 307 and a positive pressure is formed in the airflow chamber 307. At this time, the actuating body 303 is driven to displace downwardly, so that the volume of the airflow chamber 307 is shrunken and the gas inside the airflow chamber 307 is compressed and discharged out of the blast miniature pump 30. Consequently, the gas transportation is achieved by the blast miniature pump 30.

In some embodiments, the blast miniature pump 30 of the present disclosure may be a MEMS gas pump formed by a MEMS method. The nozzle plate 301, the chamber frame 302, the actuating body 303, the insulation frame 304 and the conducting frame 305 can all be made through a surface micromachining technology to reduce the volume of the blast miniature pump 30, so as to form a MEMS gas pump.

Please refer to FIG. 2, FIG. 3C and FIG. 3D. In the embodiment, the portable air quality monitoring device 1 of the present disclosure further includes a power supply module 16 for storing energy and outputting energy. In one embodiment, the power supply module 16 may be a battery module, and the power supply module 16 may transfer the energy to the air monitoring module 12, the particle detecting module 13 and the control module 15. The power supply module 16 may also receive the energy form an external power supply device 3 through a wired transmission path, and store the energy. The wired transmission path can be established by utilizing a USB transmission port, a mini-USB transmission port, or a micro-USB transmission port, so that the external power supply device 3 and the power supply module 16 could be coupled for storing energy and outputting energy. In another embodiment, the power supply module 16 may receive the energy form the external power supply device 3 through a wireless transmission path, and store the energy. For example, the power supply module 16 has a wireless charging component, so that the external power supply device 3 and the power supply module 16 could be coupled for storing energy and outputting energy through the wireless transmission path. In some embodiments, the external power supply device 3 may be a charger or a portable power bank, but not limited to.

Please refer to FIG. 2, FIG. 3C and FIG. 3D again. The control module 15 of the portable air quality monitoring device 1 of the present disclosure further includes a microprocessor 15a and a communicator 15b. The communicator 15b includes an Internet of Things (IoT) communication component 151b and a data communication component 152b. The portable air quality monitoring device 1 obtains a monitoring data by the air monitoring module 12 and the particle detecting module 13, both of which actuate every 8 seconds, by which the air quality of a location is processed, and the monitoring data is generated. The GPS component 14 is for positioning the location as the position data. The position data is received by the microprocessor 15a, and a notification data is generated thereby. The notification data is delivered to the communicator 15b, and is delivered outwardly. The monitoring data includes a volatile organic compounds (VOCs) data and a fine suspended particles (PM 2.5) data. The position data includes the address information related to the house number of the location. The address information related to the house number includes the city of the house number, the road of the house number, the section of the house number, and the number. In some embodiments, the IoT communication component 151b is a narrowband IoT device delivering signals by a narrowband radio communication technology, but not limited thereto.

In this embodiment, the method of air quality notification of the present disclosure is illustrated as FIG. 1A and FIG. 2. In the embodiment, at the step a1, the portable air quality monitoring device 1 for monitoring air quality is provided. The portable air quality monitoring device 1 obtains a monitoring data by the air monitoring module 12 and the particle detecting module 13 actuating in a monitoring period of time. In some embodiments, the monitoring period of time is regular intervals, e.g., at intervals of 5 seconds to 2 minutes. Consequently, the air quality of the location is processed and the monitoring data is generated as the monitoring data by the air monitoring module 12 and the particle detecting module 13. The GPS component 14 is for positioning the location as the position data. The position data is received by the microprocessor 15a, and a notification data is generated thereby. The notification data is delivered to the IoT communication component 151b of the communicator 15b, and is delivered outwardly. At the step a2, the notification data is received by the IoT communication component 151b, and is delivered to a cloud data processing device 4. The cloud data processing device 4 is provided for receiving the notification data delivered from the portable air quality monitoring device 1. The cloud data processing device 4 processes and calculates the notification data and converts it into a push data, and then delivers the push data at a push period through a push notification service. In some embodiments, the push period may be at regular intervals, e.g., at intervals of 5 seconds to 10 minutes. That is, the push data may be delivered every 5 seconds to 10 minutes at a time. In some other embodiments, the push period can be but not limited to at regular intervals of 5 minutes. Preferably but not exclusively, the push period may be at the regular intervals of 8 seconds. Finally, at the step a3, a notification receiving device 5 is provided for receiving the push data delivered from the cloud data processing device 4, so as to display the push data immediately. The push data may be a news report or a web news report. The web news report is broadcast through a streaming platform, e.g., YouTube, iTunes, etc. Consequently, an instant air quality map is provided, and the user can be notified to take immediate protective measures.

Figure 1B:
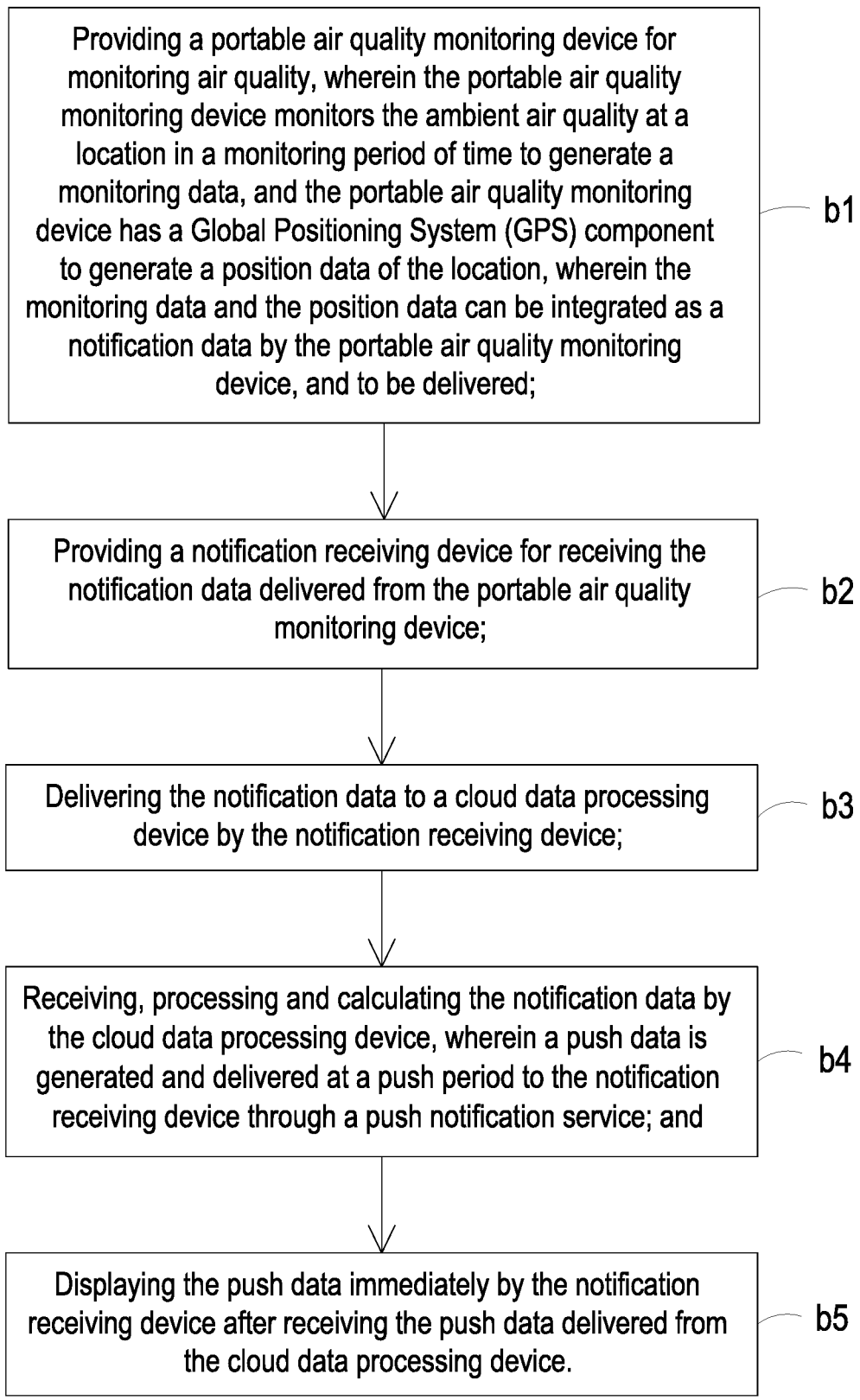
FIG. 1B is a flow chart illustrating a method of providing an air quality notification according to a second embodiment of the present disclosure.

In another embodiment, the method of air quality notification of the present disclosure is illustrated as FIG. 1B. In this embodiment, at the step b1, a portable air quality monitoring device 1 for monitoring air quality is provided. The portable air quality monitoring device 1 monitors the ambient air quality at a location in a monitoring period of time so as to generate a monitoring data. The portable air quality monitoring device 1 has a GPS component 14 to generate the position data of the location of the portable air quality monitoring device 1. The monitoring data and the position data can be integrated to a notification data, and to be delivered. At the step b2, a notification receiving device 5 is provided for receiving the notification data delivered from the portable air quality monitoring device 1. At the step b3, the notification receiving device 5 delivers the notification data to the cloud data processing device 4. At the step b4, the cloud data processing device 4 receives the notification data, after processing and calculating the notification data, the notification data is converted into a push data. The push data is then delivered at a push period through a push notification service. Finally, at the step b5, the notification receiving device 5 receives the push data delivered from the cloud data processing device 4, so as to display the push data immediately. Consequently, an instant air quality map is provided, and the user can be notified to take immediate protective measures.

Please refer to FIG. 1B and FIG. 2. In this embodiment, at the step b1, the portable air quality monitoring device 1 obtains the monitoring data by the air monitoring module 12 and the particle detecting module 13 actuating in the monitoring period of time. In some embodiments, the monitoring period of time is at regular intervals, e.g., at intervals of 5 seconds to 2 minutes. In the meantime, the GPS component 14 of the portable air quality monitoring device 1 generates the position data of the location. The monitoring data and the position data are received by the microprocessor 15a, and a notification data is generated thereby. The notification data is delivered to the data communication component 152b of the communicator 15b, and is delivered outwardly. At the step b2, the notification receiving device 5 is provided for receiving the notification data delivered from the portable air quality monitoring device 1. At the step b3, the notification receiving device 5 delivers the notification data to the cloud data processing device 4. At the step b4, the cloud data processing device 4 receives the notification data for storing, recording, processing and calculating the notification data. After that, the notification data is converted into the push data, which is then delivered at the push period through the push notification service. In some embodiments, the push period may be at regular intervals, e.g., at intervals of 5 seconds to 10 minutes. In some other embodiments, the push period can be but not limited to at regular intervals of 5 minutes. Preferably but not exclusively, the push period may be at the regular intervals of 8 seconds. Finally, at the step b5, the notification receiving device 5 receives the push data delivered from the cloud data processing device 4, so as to display the push data immediately. In some embodiments, the push data may be a news report or a web news report. The web news report is broadcast through a streaming platform (e.g., YouTube, iTunes, etc.) or a community website (e.g., Facebook, Instagram, etc.). Consequently, the instant air quality map is provided, and the user can be notified to take immediate protective measures. In one embodiment, the data communication component 152b may deliver the notification data through a wired transmission path. The wired transmission path can be established by utilizing a USB transmission port, a mini-USB transmission port, or a micro-USB transmission port. In another embodiment, the data communication component 152b may deliver the notification data through a wireless transmission path. The wireless communication transmission path can be established by utilizing a Wifi communication technology, a Bluetooth communication technology, an RF communication technology, or a Zigbee communication technology.

In some embodiments, the notification receiving device 5 can be a mobile communication device, such as a mobile phone, a notebook, a tablet computer, or a wearable device, e.g., intelligent watch, intelligent wristband, etc.

In summary, the present disclosure provides a method of air quality notification for monitoring air quality by a portable air quality monitoring device. The portable air quality monitoring device monitors the ambient air quality at a location in a monitoring period of time so as to generate a monitoring data. The portable air quality monitoring device has a Global Positioning System (GPS) component to generate the position data of the location of the portable air quality monitoring device. The monitoring data and the position data can be integrated as a notification data by the portable air quality monitoring device, and to be delivered. A cloud data processing device is provided for receiving the notification data, processing, calculating and converting the notification, so that a push data is generated and then delivered at a push period to a notification receiving device through a push notification service. Consequently, the notification receiving device is capable of receiving 3600 air quality information of the address information related to the house number of the location within 8 hours. Meanwhile, the air quality information can be delivered to the user through the push notification service. In this circumstance, the instant air quality map is provided, and the user can be notified to take immediate protective measures to avoid the gas poisoning and the gas explosion.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method of air quality notification, comprising steps of:
    (a1) providing a portable air quality monitoring device for monitoring air quality, wherein the portable air quality monitoring device monitors the ambient air quality at a location in a monitoring period of time to generate a monitoring data, and the portable air quality monitoring device has a Global Positioning System (GPS) component to generate a position data of the location, wherein the monitoring data and the position data can be integrated as a notification data by the portable air quality monitoring device, and to be delivered, wherein the portable air quality monitoring device further comprises an air monitoring module and a particle detecting module for monitoring air quality and providing the monitoring data, wherein the monitoring data comprises a volatile organic compounds (VOCs) data and a fine suspended particles (PM 2.5) data;
    (a2) providing a cloud data processing device for receiving the notification data delivered from the portable air quality monitoring device, wherein the notification data is processed, calculated and converted to generate a push data, and the push data is delivered at a push period through a push notification service; and
    (a3) providing a notification receiving device for receiving the push data delivered from the cloud data processing device, so as to display the push data immediately.

2. The method according to claim 1, wherein the monitoring period of time is at regular intervals of 5 seconds to 2 minutes.

3. The method according to claim 1, wherein the position data comprises address information related to a house number of the location, and the address information related to the house number comprises the city of the house number, the road of the house number, the section of the house number, and the number.

4. The method according to claim 1, wherein the push period is at regular intervals of 5 seconds to 10 minutes.

5. The method according to claim 4, wherein the push period is at regular intervals of 8 seconds.

6. The method according to claim 4, wherein the push period is at regular intervals of 5 minutes.

7. The method according to claim 1, wherein the air monitoring module comprises a gas sensor and a gas actuator, wherein the gas actuator inhales the gas into the air monitoring module and to be sensed by the gas sensor, so as to obtain the VOCs data, and the particle detecting module comprises a fine particle actuator and a fine particle sensor, wherein the fine particle actuator inhales the gas into the particle detecting module and to be sensed by the fine particle sensor, so as to obtain the PM 2.5 data.

8. The method according to claim 7, wherein the gas actuator and the fine particle actuator are blast miniature pumps, wherein each of the blast miniature pump comprises:
    a nozzle plate having a plurality of brackets, a suspension plate and a central aperture, wherein the suspension plate is permitted to undergo a bending vibration, the plurality of brackets are connected to the periphery of the suspension plate for providing an elastic support, the central aperture is formed at a central position of the suspension plate, and the blast miniature pump is fixedly disposed by the plurality of brackets, and an airflow chamber is formed under the bottom of the nozzle plate, and at least one vacant space is formed among the suspension plate and the brackets;
    a chamber frame stacked on the suspension plate;
    an actuating body stacked on the chamber frame, wherein when a voltage is applied, the suspension plate is driven to undergo the bending vibration;
    an insulation frame stacked on the actuating body; and
    a conducting frame stacked on the insulation frame;
    wherein, a resonance chamber is formed among the actuating body, the chamber frame and the suspension plate, when the actuating body is actuated by an applied voltage, the actuating body is deformed, and the nozzle plate is simultaneously driven to vibrate, whereby the suspension plate is driven to undergo the displaced vibration, so that the gas is transported into the airflow chamber through the at least one vacant space and discharged to achieve the gas transportation.

9. The method according to claim 7, wherein the gas actuator and the fine particle actuator are micro-electromechanical-systems (MEMS) gas pumps.

10. The method according to claim 1, wherein the portable air quality monitoring device further comprises a control module, the control module comprises a microprocessor and a communicator, wherein the communicator comprises an Internet of Things (IoT) communication component for receiving the notification data and delivering it to the cloud data processing device to be received, stored, recorded and processed, so as to generate the push data.

11. The method according to claim 1, wherein the notification receiving device is a mobile communication device, and the mobile communication device is at least one selected from the group consisting of a mobile phone, a notebook, a tablet computer, an intelligent watch and an intelligent wristband.

12. The method according to claim 1, wherein the push data is a news report or a web news report.

13. The method according to claim 12, wherein the web news report is broadcast through a streaming platform or a community website.

14. A method of air quality notification, comprising steps of:
(b1) providing a portable air quality monitoring device for monitoring air quality, wherein the portable air quality monitoring device monitors the ambient air quality at a location in a monitoring period of time to generate a monitoring data, and the portable air quality monitoring device has a Global Positioning System (GPS) component to generate a position data of the location, wherein the monitoring data and the position data can be integrated as a notification data by the portable air quality monitoring device, and to be delivered, wherein the portable air quality monitoring device further comprises an air monitoring module and a particle detecting module for monitoring air quality and providing the monitoring data, wherein the monitoring data comprises a volatile organic compounds (VOCs) data and a fine suspended particles (PM 2.5) data;
(b2) providing a notification receiving device for receiving the notification data delivered from the portable air quality monitoring device;
(b3) delivering the notification data to a cloud data processing device by the notification receiving device;
(b4) receiving, processing and calculating the notification data by the cloud data processing device, wherein a push data is generated and delivered at a push period to the notification receiving device through a push notification service; and
(b5) displaying the push data immediately by the notification receiving device after receiving the push data delivered from the cloud data processing device.

15. The method according to claim 14, wherein the monitoring period of time is at regular intervals of 5 seconds to 2 minutes.

16. The method according to claim 14, wherein the position data comprises an address information related to a house number of the location, and the address information related to the house number comprises the city of the house number, the road of the house number, the section of the house number, and the number.

17. The method according to claim 14, wherein the push period is at regular intervals of 5 seconds to 10 minutes.

18. The method according to claim 17, wherein the push period is at regular intervals of 8 seconds.

19. The method according to claim 17, wherein the push period is at regular intervals of 5 minutes.

* * * * *